(12) United States Patent
Hazlett

(10) Patent No.: US 10,500,222 B2
(45) Date of Patent: Dec. 10, 2019

(54) COMPOSITIONS AND METHODS RELATING TO TREATMENT OF INFECTION

(71) Applicant: Wayne State University, Detroit, MI (US)

(72) Inventor: Linda D. Hazlett, Grosse Pointe Park, MI (US)

(73) Assignee: Wayne State University, Detroit, MI (US)

( * ) Notice: Subject to any disclaimer, the term of this patent is extended or adjusted under 35 U.S.C. 154(b) by 4 days.

(21) Appl. No.: 15/297,438

(22) Filed: Oct. 19, 2016

(65) Prior Publication Data
US 2017/0106007 A1   Apr. 20, 2017

Related U.S. Application Data

(60) Provisional application No. 62/243,388, filed on Oct. 19, 2015.

(51) Int. Cl.
*A61K 31/704* (2006.01)
*A61K 45/06* (2006.01)
*A61K 9/00* (2006.01)
*A61K 9/08* (2006.01)

(52) U.S. Cl.
CPC .......... *A61K 31/704* (2013.01); *A61K 9/0048* (2013.01); *A61K 45/06* (2013.01); *A61K 9/0051* (2013.01); *A61K 9/08* (2013.01)

(58) Field of Classification Search
CPC .... A61K 31/704; A61K 45/06; A61K 9/0048; A61K 9/08; A61K 9/0051; A61K 2300/00
USPC .......................................................... 514/23
See application file for complete search history.

(56) References Cited

U.S. PATENT DOCUMENTS 8,858,964 B2 * 10/2014 Vournakis ............ A61K 9/0014
                                                        424/400
2008/0004236 A1 * 1/2008 Comper ................ A61K 31/737
                                                        514/54

FOREIGN PATENT DOCUMENTS

JP        2005247796 A  *  9/2005  ............... A61K 9/08

OTHER PUBLICATIONS

The Merck Manual, 1992, pp. 146-150.*
Kondratenko et al, Pharmaceutical Chemistry Journal, 2003, 37 (9), 485-488.*
McClellan et al, J. Immunol., Feb. 15, 2015, 194(4), 1776-1787.*
Mollica et al, Chemistry & Biology, Apr. 2007, 14, 431-441.*
Eifrig et al, Ophthalmology, 2003, 110, 1714-1717.*
Davis, E. et al. Medicinal uses of licorice through the millennia: the good and plenty of it, Mol Cell Endocrinol, 78:1-6, 1991.
McClellan, S. et al., High-mobility group box 1: a novel target for treatment of Pseudomonas aeruginosa keratitis, J Immunol, 194: 1776-1787, 2015.
Messier, C. et al., Licorice and its Potential Beneficial Effects in Common Oro-Dental Diseases, *Oral Dis.*,18(1):32-9, Jan. 2012.
Messier, C. et al., Effect of licorice compounds licochalcone A, glabridin and glycyrrhizic acid on growth and virulence properties of Candida albicans, Mycoses, 54(6): e801-6, Nov. 2011.
Mollica, L. et al., Glycyrrhizin binds to high-mobility group box 1 protein and inhibits its cytokine activities, Chem Biol, 14: 431-441, 2007.
Shen, L. et al., Anti-inflammative effect of glycyrrhizin on rat thermal injury via inhibition of high-mobility group box 1 protein, Burns, 41: 372-378, 2015.
Zhang, J. et al., Glycyrrhizin protects brain against ischemia reperfusion injury in mice through HMGB1-TLR4-IL-17A signaling pathway, Brain Res, 1582: 176-186, 2014.

* cited by examiner

*Primary Examiner* — Ganapathy Krishnan
(74) *Attorney, Agent, or Firm* — Julie K. Staple; Dinsmore & Shohl LLP

(57) ABSTRACT

Microbial keratitis is a sight threatening disorder and infections result in ocular pain, stromal destruction, corneal thinning and/or perforation, leading to vision loss, if untreated and the need for transplantation. Methods of treating bacterial infection of the cornea prophylactically or therapeutically in a subject, are provided according to aspects of the present invention which include administering an effective dose of glycyrrhizin, or a pharmaceutically acceptable salt, hydrate, solvate, ester, amide, isomer or derivative thereof characterized by anti-bacterial activity, to the subject.

9 Claims, 18 Drawing Sheets

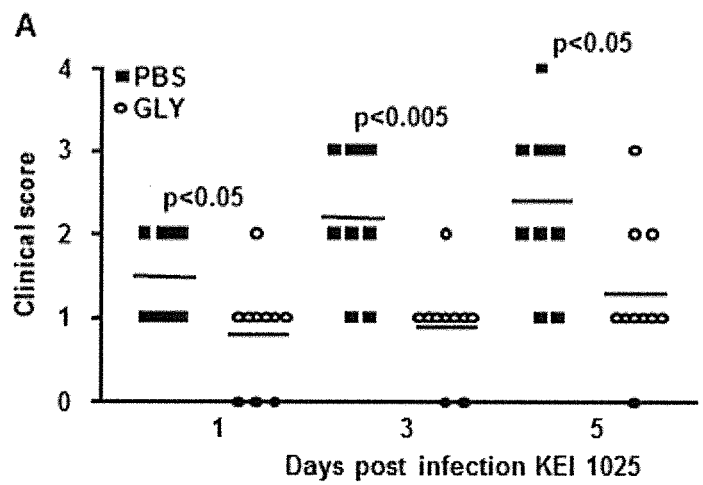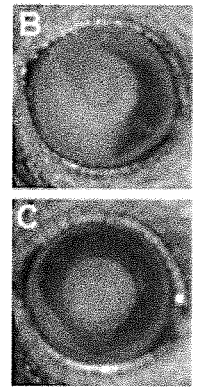
FIG. 1A
FIG. 1B
FIG. 1C
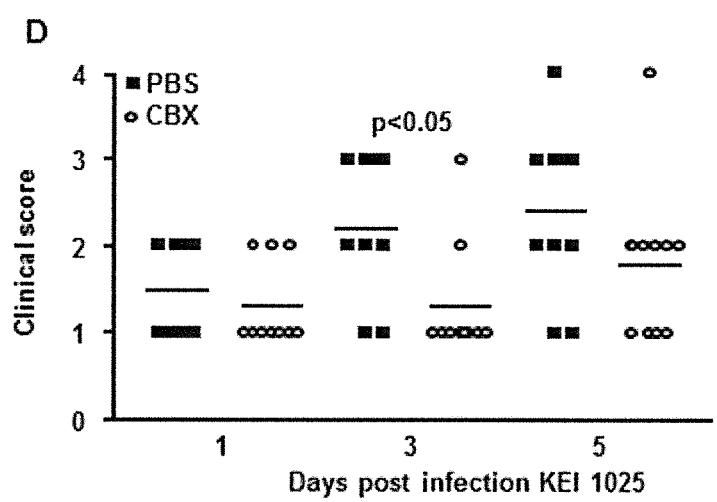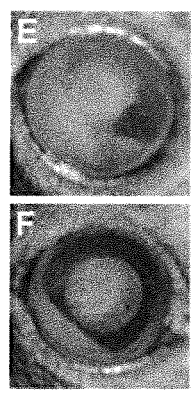
FIG. 1D
FIG. 1E
FIG. 1F

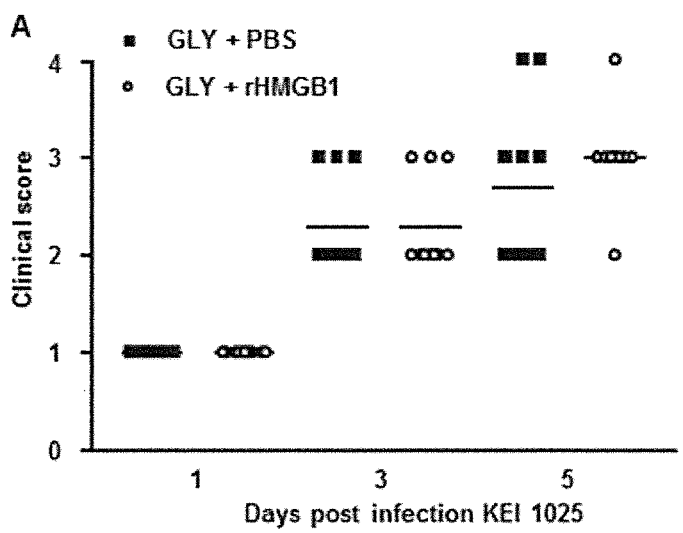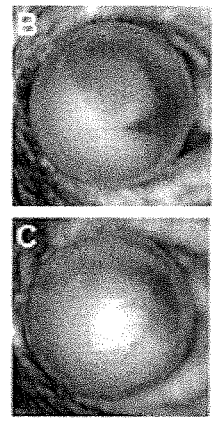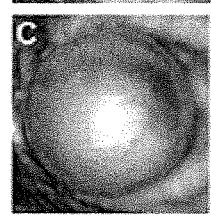
FIG. 8A
FIG. 8B
FIG. 8C
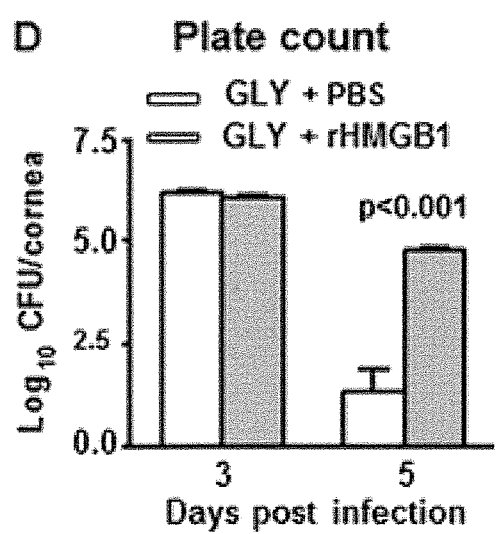
FIG. 8D

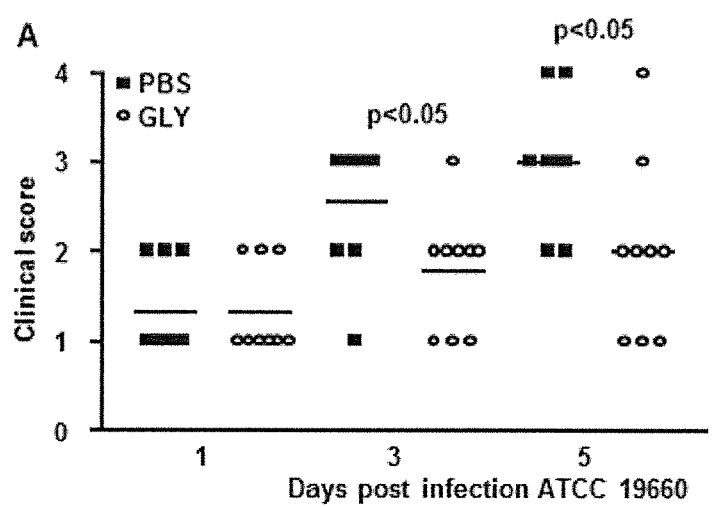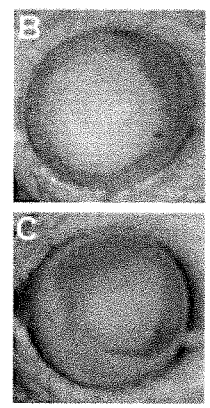
FIG. 9B
FIG. 9C
FIG. 9A

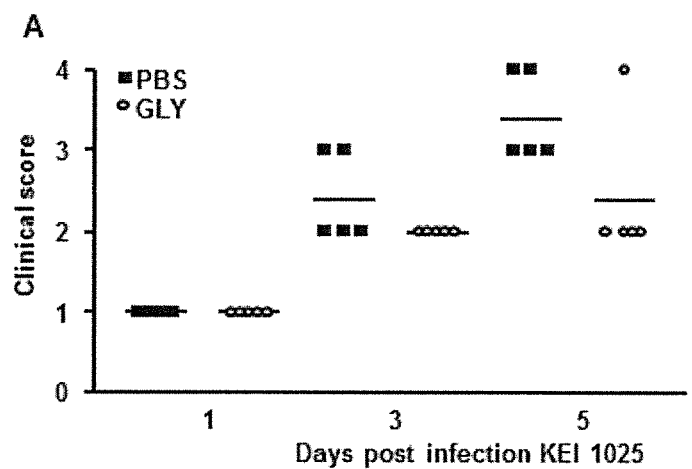
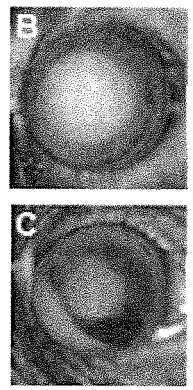
FIG. 11B
FIG. 11C
FIG. 11A
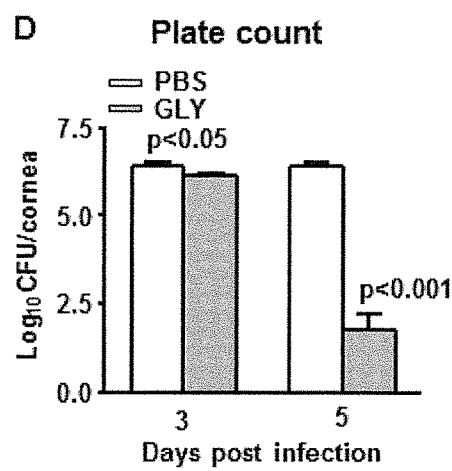
FIG. 11D

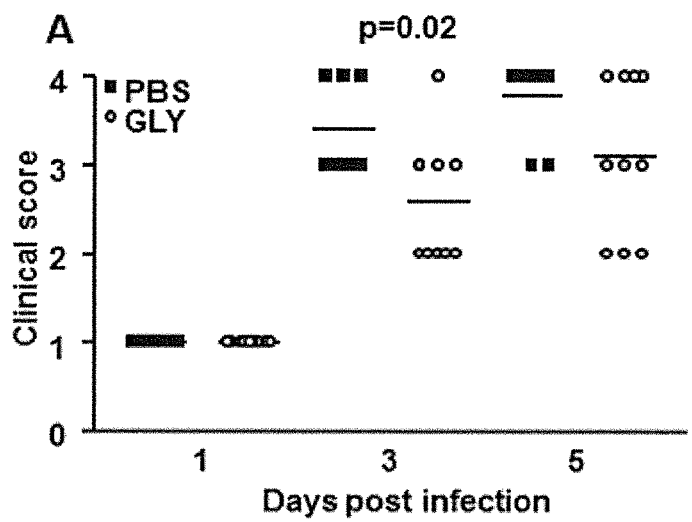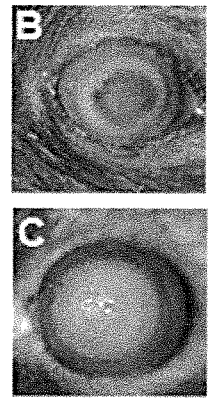
FIG. 13B
FIG. 13C
FIG. 13A
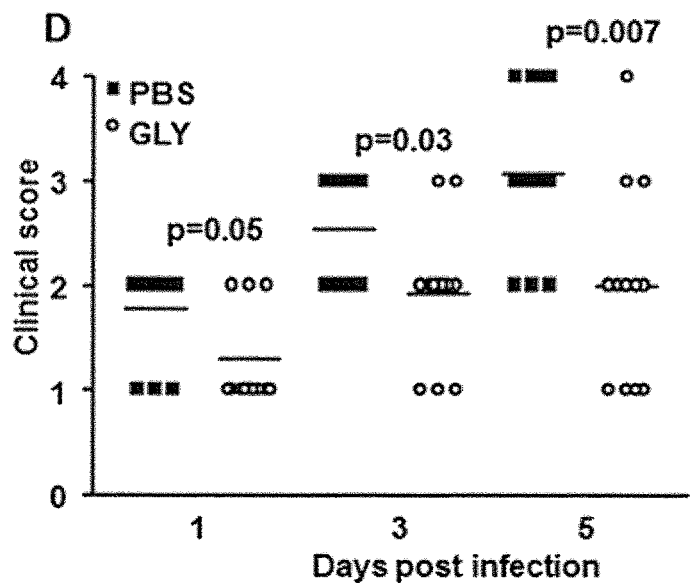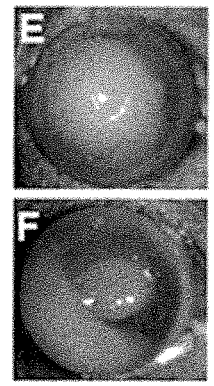
FIG. 13E
FIG. 13F
FIG. 13D

COMPOSITIONS AND METHODS RELATING TO TREATMENT OF INFECTION

REFERENCE TO RELATED APPLICATION

This application claims priority to U.S. Provisional Patent Application Ser. No. 62/243,388, filed Oct. 19, 2015, the entire content of which is incorporated herein by reference.

GRANT REFERENCE

This invention was made with government support under Contract No. R01 EY016058, awarded by the National Institutes of Health. The Government has certain rights in the invention.

FIELD OF THE INVENTION

This disclosure relates generally to compositions and methods for treating bacterial infections, such as *Pseudomonas* (P.) *aeruginosa* infections, prophylactically or therapeutically. According to specific aspects, methods of treating bacterial infections to the cornea, such as *P. aeruginosa* infections of the cornea, prophylactically or therapeutically, including administration of glycyrrhizin, or a pharmaceutically acceptable salt, hydrate, solvate, ester, amide, isomer or derivative thereof to a subject, are provided herein.

BACKGROUND OF THE INVENTION

Microbial keratitis is a sight threatening disorder associated with multiple risk factors, including use of extended wear contact lenses, ocular surface disease, ocular surgery, immunosuppression and traumatic ocular surface events, particularly prevalent in developing countries. Among pathogens, the Gram-negative bacterium, *Pseudomonas aeruginosa* (*P. aeruginosa*) remains a leading cause of contact lens induced microbial keratitis, and infections result in ocular pain, stromal destruction, corneal thinning and/or perforation, leading to vision loss, if untreated.

Intensive antibiotic therapy is used to treat the disease, but with emerging antibiotic resistance of *P. aeruginosa* and other pathogens, there is a continuing need for compositions and methods for prophylactic or therapeutic treatment of bacterial infections, such as *P. aeruginosa* infections.

SUMMARY OF THE INVENTION

Methods of treating *Pseudomonas aeruginosa* infection of the cornea prophylactically or therapeutically in a subject are provided according to aspects of the present invention which include administering an effective dose of glycyrrhizin, or a pharmaceutically acceptable salt, hydrate, solvate, ester, amide, isomer or derivative thereof, to the subject, thereby treating *Pseudomonas aeruginosa* infection of the cornea prophylactically or therapeutically in the subject.

According to aspects of methods of the present invention, the subject is human. According to aspects of methods of the present invention, the subject is a horse.

Administering the effective dose of glycyrrhizin, or a pharmaceutically acceptable salt, hydrate, solvate, ester, amide, isomer or derivative thereof, includes subconjunctival administration, topical administration to the cornea, systemic administration, parenteral administration, or a combination of any two or more thereof.

Administering the effective dose of glycyrrhizin, or a pharmaceutically acceptable salt, hydrate, solvate, ester, amide, isomer or derivative thereof, includes subconjunctival administration, topical administration to the cornea, intravenous administration, parenteral administration, or a combination of any two or more thereof.

Optionally an additional therapeutic agent is administered to the subject to aid in treating a *Pseudomonas aeruginosa* infection of the cornea prophylactically or therapeutically in the subject.

Methods of treating *Pseudomonas aeruginosa* infection of the cornea prophylactically or therapeutically in a subject are provided according to aspects of the present invention which include administering an effective dose of glycyrrhizin, or a pharmaceutically acceptable salt, hydrate, solvate, ester, amide, isomer or derivative thereof, and an effective dose of an antibiotic to the subject, thereby treating *Pseudomonas aeruginosa* infection of the cornea prophylactically or therapeutically in the subject.

Methods of treating *Pseudomonas aeruginosa* infection of the cornea prophylactically or therapeutically in a subject are provided according to aspects of the present invention which include administering an effective dose of glycyrrhizin, or a pharmaceutically acceptable salt, hydrate, solvate, ester, amide, isomer or derivative thereof, and an effective dose of an additional therapeutic agent selected from the group consisting of: an antibiotic, an antiviral, an analgesic, an antipyretic, an anti-inflammatory agent, a non-steroidal anti-inflammatory agent, a steroid, and a combination of any two or more thereof, to the subject, thereby treating *Pseudomonas aeruginosa* infection of the cornea prophylactically or therapeutically in the subject.

Methods of treating *Pseudomonas aeruginosa* infection of the cornea prophylactically or therapeutically in a subject are provided according to aspects of the present invention which include administering an effective dose of glycyrrhizin, or a pharmaceutically acceptable salt, hydrate, solvate, ester, amide, isomer or derivative thereof, to the subject within 24 hours of a traumatic ocular surface event thereby treating *Pseudomonas aeruginosa* infection of the cornea prophylactically or therapeutically in the subject.

Methods of treating *Pseudomonas aeruginosa* infection of the cornea prophylactically or therapeutically in a subject are provided according to aspects of the present invention which include administering an effective dose of glycyrrhizin, or a pharmaceutically acceptable salt, hydrate, solvate, ester, amide, isomer or derivative thereof, to the subject within 8 hours of a traumatic ocular surface event thereby treating *Pseudomonas aeruginosa* infection of the cornea prophylactically or therapeutically in the subject.

Methods of treating *Pseudomonas aeruginosa* infection of the cornea prophylactically or therapeutically in a subject are provided according to aspects of the present invention which include administering an effective dose of glycyrrhizin, or a pharmaceutically acceptable salt, hydrate, solvate, ester, amide, isomer or derivative thereof, to the subject within 6 hours of a traumatic ocular surface event thereby treating *Pseudomonas aeruginosa* infection of the cornea prophylactically or therapeutically in the subject.

Methods of treating a bacterial infection in a subject prophylactically or therapeutically, are provided according to aspects of the present invention which include administering a combination of: 1) an effective dose of glycyrrhizin, or a pharmaceutically acceptable salt, hydrate, solvate, ester, amide, isomer or derivative thereof; and 2) an effective dose of one or more additional therapeutic agents, to the subject, thereby treating the bacterial infection in a subject prophylactically or therapeutically.

Methods of treating a bacterial infection in a subject prophylactically or therapeutically, are provided according to aspects of the present invention wherein the bacterial infection is *Pseudomonas aeruginosa*-mediated keratitis and administering the effective dose of glycyrrhizin, or a pharmaceutically acceptable salt, hydrate, solvate, ester, amide, isomer or derivative thereof; and the effective dose of the one or more additional therapeutic agents comprises topical administration of the glycyrrhizin, or a pharmaceutically acceptable salt, hydrate, solvate, ester, amide, isomer or derivative thereof and the one or more additional therapeutic agents to a cornea of the subject.

Methods of treating a bacterial infection in a subject prophylactically or therapeutically, are provided according to aspects of the present invention wherein the bacterial infection is *Pseudomonas aeruginosa*-mediated keratitis and administering the effective dose of glycyrrhizin, or a pharmaceutically acceptable salt, hydrate, solvate, ester, amide, isomer or derivative thereof; and the effective dose of the one or more additional therapeutic agents comprises systemic administration of the glycyrrhizin, or a pharmaceutically acceptable salt, hydrate, solvate, ester, amide, isomer or derivative thereof and the one or more additional therapeutic agents to the subject.

Methods of treating a bacterial infection in a subject prophylactically or therapeutically, are provided according to aspects of the present invention wherein the bacterial infection is *Pseudomonas aeruginosa*-mediated keratitis and administering the effective dose of glycyrrhizin, or a pharmaceutically acceptable salt, hydrate, solvate, ester, amide, isomer or derivative thereof; and the effective dose of the one or more additional therapeutic agents comprises subconjunctival administration of the glycyrrhizin, or a pharmaceutically acceptable salt, hydrate, solvate, ester, amide, isomer or derivative thereof and the one or more additional therapeutic agents to a cornea of the subject.

Compositions formulated for topical administration to the cornea for treating a bacterial infection of the cornea, such as, but not limited to, an eyedrop, spray, ointment, or gel formulation, in a subject prophylactically or therapeutically, are provided according to aspects of the present invention which include glycyrrhizin, or a pharmaceutically acceptable salt, hydrate, solvate, ester, amide, isomer or derivative thereof.

Compositions for treating a bacterial infection in a subject prophylactically or therapeutically, are provided according to aspects of the present invention which include glycyrrhizin, or a pharmaceutically acceptable salt, hydrate, solvate, ester, amide, isomer or derivative thereof; an additional therapeutic agent, such as but not limited to, an antibiotic, an antiviral, an analgesic, an antipyretic, an anti-inflammatory agent, a non-steroidal anti-inflammatory agent, a steroid, thrombomodulin or a combination of any two or more thereof; and a pharmaceutically acceptable carrier.

BRIEF DESCRIPTION OF THE DRAWINGS

FIG. 1A illustrates that clinical scores were reduced significantly at 1, 3 and 5 days post-infection (p.i.) with *Pseudomonas aeruginosa* in glycyrrhizin (GLY) treated mice compared to mice treated with phosphate buffered saline (PBS);

FIG. 1B is an image of a mouse eye treated with PBS, at 5 days p.i.;

FIG. 1C is an image of a mouse eye treated with GLY, at 5 days p.i.; (00251 FIG. 1D illustrates that clinical scores were only reduced at 3 days post-infection (p.i.) after infection with *Pseudomonas aeruginosa* in carbenoxolone (CBX) treated mice compared to mice treated with phosphate buffered saline (PBS);

FIG. 1E is an image of a mouse eye treated with PBS, at 5 days p.i.;

FIG. 1F is an image of a mouse eye treated with CBX, at 5 days p.i.;

FIG. 8A is a graph showing clinical scores at 1, 3 and 5 days post-infection with *Pseudomonas aeruginosa* in glycyrrhizin/PBS (GLY+PBS) treated mice compared to mice treated with GLY and recombinant HMBG1 (GLY+rHMGB1);

FIG. 8B is an image of a mouse eye treated with GLY+PBS;

FIG. 8C is an image of a mouse eye treated with GLY+rHMGB1;

FIG. 8D is a graph showing the results of plate count showing bacterial load in corneas after infection of corneas with *Pseudomonas aeruginosa* and treatment with glycyrrhizin/PBS (GLY+PBS) (white bars) or GLY and recombinant HMBG1 (GLY+rHMGB1); (gray bars);

FIG. 9A is a graph showing clinical scores at 1, 3 and 5 days post-infection (p.i.) with *Pseudomonas aeruginosa* in glycyrrhizin (GLY) treated mice compared to mice treated with phosphate buffered saline (PBS);

FIG. 9B is an image of a mouse eye treated with PBS;

FIG. 9C is an image of a mouse eye treated with GLY;

FIG. 11A is a graph showing clinical scores at 1, 3 and 5 days post-infection (p.i.) of corneas with *Pseudomonas aeruginosa* in glycyrrhizin (GLY) treated mice subconjunctivally treated at 6 hours p.i. and with intraperitoneal injections at 1 and 3 days p.i. compared to mice treated with phosphate buffered saline (PBS);

FIG. 11B is an image of a mouse eye treated with PBS;

FIG. 11C is an image of a mouse eye treated with GLY;

FIG. 11D is a graph showing the results of plate count showing bacterial load in the cornea after infection with *Pseudomonas aeruginosa* and treatment with PBS (white bars) or GLY (gray bars);

FIG. 13A is a graph showing clinical scores, at 1, 3 and 5 days post-infection (p.i.) of the cornea with *Pseudomonas aeruginosa*, of mice treated topically with GLY beginning at 8 hours and at days 1-4 (×2 each day) post-infection compared to mice treated with phosphate buffered saline (PBS);

FIG. 13B is an image at 5 days p.i. of the cornea with *Pseudomonas aeruginosa* of a mouse eye treated topically with PBS beginning at 8 hours and at days 1-4 (×2 each day) post-infection;

FIG. 13C is an image at 5 days p.i. of the cornea with *Pseudomonas aeruginosa* of a mouse eye treated topically with GLY beginning at 8 hours and at days 1-4 (×2 each day) post-infection;

FIG. 13D is a graph showing clinical scores at 1, 3 and 5 days post-infection (p.i.) of the cornea with *Pseudomonas aeruginosa* of mice treated topically with GLY beginning at 6 hours and at days 1-4 (×2 each day) post-infection compared to mice treated with phosphate buffered saline (PBS);

FIG. 13E is an image at 5 days p.i. of the cornea with *Pseudomonas aeruginosa* of a mouse eye treated topically with PBS beginning at 6 hours and at days 1-4 (×2 each day) post-infection;

FIG. 13F is an image at 5 days p.i. of the cornea with *Pseudomonas aeruginosa* of a mouse eye treated topically with GLY beginning at 6 hours and at days 1-4 (×2 each day) post-infection;

DETAILED DESCRIPTION OF THE INVENTION

Figure 2A:
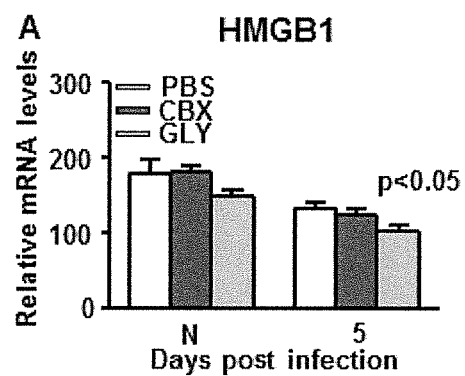
FIG. 2A is a graph showing relative HMGB1 mRNA levels in cornea analyzed by real-time RT-PCR after infection of corneas with *Pseudomonas aeruginosa* and treatment with PBS, CBX or GLY.
Figure 2B:
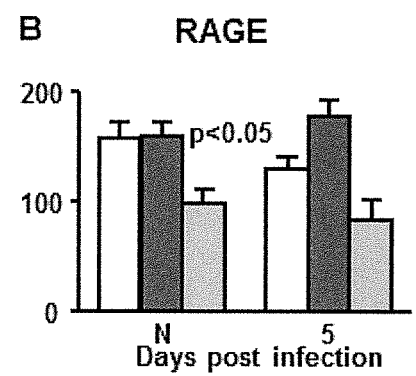
FIG. 2B is a graph showing relative RAGE mRNA levels in cornea analyzed by real-time RT-PCR after infection of corneas with *Pseudomonas aeruginosa* and treatment with PBS, CBX or GLY.

Scientific and technical terms used herein are intended to have the meanings commonly understood by those of ordinary skill in the art. Such terms are found defined and used in context in various standard references illustratively including D. L. Nelson and M. M. Cox, Lehninger Principles of Biochemistry, 4th Ed., W.H. Freeman & Company, 2004; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

Methods of treating bacterial infection of the cornea prophylactically or therapeutically in a subject, are provided according to aspects of the present invention which include administering an effective dose of glycyrrhizin, or a pharmaceutically acceptable salt, hydrate, solvate, ester, amide, isomer or derivative thereof characterized by anti-bacterial activity, to the subject.

The term "prophylactically" as used herein refers to treating a subject at high risk of bacterial infection of the cornea due to one or more risk factors associated with bacterial infection of the cornea, including, but not limited to, use of extended wear contact lenses, ocular surface disease, ocular surgery, immunosuppression, employment in an environment known to increase likelihood of contact between the cornea and soil, such as agricultural workers, and recent or likely traumatic ocular surface events. Treating prophylactically is effective to reduce bacterial load when infection does occur and ameliorates signs and symptoms of bacterial infection of the cornea.

The term "traumatic ocular surface event" refers to events which cause introduction of foreign material onto or into the cornea, such as a scratch, abrasion, nick, gouge, tear, cut or surgical incision of the cornea.

The term "therapeutically" as used herein refers to treating a subject having a bacterial infection of the cornea. Treating therapeutically is effective to reduce bacterial load in an infected cornea and ameliorates signs and symptoms of bacterial infection of the cornea.

Glycyrrhizin (GLY) is a glycoconjugated triterpene. Its 18β glycyrrhetinic acid moiety binds high mobility group box-1 (HMGB1).

Methods of treating a *Pseudomonas aeruginosa* infection of the cornea prophylactically or therapeutically in a subject, are provided according to aspects of the present invention which include administering an effective dose of glycyrrhizin, or a pharmaceutically acceptable salt, hydrate, solvate, ester, amide, isomer or derivative thereof characterized by anti-*Pseudomonas aeruginosa* activity, to the subject, thereby treating a *Pseudomonas aeruginosa* infection of the cornea prophylactically or therapeutically in a subject.

According to aspects of the present invention, the subject has or is susceptible to *Pseudomonas aeruginosa*-mediated keratitis.

Glycyrrhizin, or a pharmaceutically acceptable salt, hydrate, solvate, ester, amide, isomer or derivative thereof characterized by anti-bacterial activity, is administered to a subject by a variety of systemic and/or local routes including, but not limited to, intravenous, intramuscular, subcutaneous, intraperitoneal, oral, otic, rectal, vaginal, topical, parenteral, pulmonary, ocular, nasal and mucosal, depending on the location of the infection to be treated. According to particular aspects, glycyrrhizin, or a pharmaceutically acceptable salt, hydrate, solvate, ester, amide, isomer or derivative thereof characterized by anti-bacterial activity, particularly anti-*Pseudomonas aeruginosa* activity, is administered to treat a corneal infection, by administration to the cornea locally or systemically, such as, but not limited to, topical administration to the cornea, subconjunctival administration, intravenous administration, or a combination of two or more thereof.

According to aspects of the present invention, the subject has or is susceptible to *Pseudomonas aeruginosa*-mediated keratitis and administering the effective dose of glycyrrhizin, or a pharmaceutically acceptable salt, hydrate, solvate, ester, amide, isomer or derivative thereof characterized by anti-*Pseudomonas aeruginosa* activity, includes topical administration of glycyrrhizin, or a pharmaceutically acceptable salt, hydrate, solvate, ester, amide, isomer or derivative thereof characterized by anti-*Pseudomonas aeruginosa* activity, to the cornea.

According to aspects of the present invention, the subject has or is susceptible to *Pseudomonas aeruginosa*-mediated keratitis and administering the effective dose of glycyrrhizin, or a pharmaceutically acceptable salt, hydrate, solvate, ester, amide, isomer or derivative thereof characterized by anti-*Pseudomonas aeruginosa* activity, includes subconjunctival administration of glycyrrhizin, or a pharmaceutically acceptable salt, hydrate, solvate, ester, amide, isomer or derivative thereof characterized by anti-*Pseudomonas aeruginosa* activity.

According to aspects of the present invention, the subject has or is susceptible to *Pseudomonas aeruginosa*-mediated keratitis and administering the effective dose of glycyrrhizin, or a pharmaceutically acceptable salt, hydrate, solvate, ester, amide, isomer or derivative thereof characterized by anti-*Pseudomonas aeruginosa* activity, includes systemic administration of glycyrrhizin, or a pharmaceutically acceptable salt, hydrate, solvate, ester, amide, isomer or derivative thereof characterized by anti-*Pseudomonas aeruginosa* activity.

According to aspects of the present invention, the subject has or is susceptible to *Pseudomonas aeruginosa*-mediated keratitis and administering the effective dose of glycyrrhizin, or a pharmaceutically acceptable salt, hydrate, solvate, ester, amide, isomer or derivative thereof characterized by anti-*Pseudomonas aeruginosa* activity, includes parenteral administration of glycyrrhizin.

According to aspects of the present invention, the subject has or is susceptible to *Pseudomonas aeruginosa*-mediated keratitis and administering the effective dose of glycyrrhizin, or a pharmaceutically acceptable salt, hydrate, solvate, ester, amide, isomer or derivative thereof characterized by anti-*Pseudomonas aeruginosa* activity, includes intravenous administration of glycyrrhizin.

Glycyrrhizin, or a pharmaceutically acceptable salt, hydrate, solvate, ester, amide, isomer or derivative thereof characterized by anti-*Pseudomonas aeruginosa* activity, is administered by two or more routes of administration to treat *Pseudomonas aeruginosa*-mediated keratitis prophylactically or therapeutically according to aspects of the present invention, specifically, subconjunctival and topical administration to the cornea; subconjunctival and intravenous administration; topical administration to the cornea and intravenous administration; or subconjunctival administration, topical administration to the cornea and intravenous administration.

Methods of treating a *Pseudomonas aeruginosa* infection in a subject prophylactically or therapeutically, are provided according to aspects of the present invention which include administering an effective dose of glycyrrhizin, or a pharmaceutically acceptable salt, hydrate, solvate, ester, amide, isomer or derivative thereof characterized by anti-*Pseudomonas aeruginosa* activity, to the subject, wherein the *Pseudomonas aeruginosa* infection is or includes infection with a cytotoxic strain of *Pseudomonas aeruginosa*, a non-cytotoxic strain of *Pseudomonas aeruginosa* or a combination of a cytotoxic strain of *Pseudomonas aeruginosa* and a non-cytotoxic strain of *Pseudomonas aeruginosa*.

Cytotoxicity of *Pseudomonas aeruginosa* isolates is well-characterized as causing death of epithelial cells when incubated with them, see for example, Evans et al., Infect Immun. 1998 April, 66(4): 1453-1459; and Rabin and Hauser, ExoU: A cytotoxin delivered by the type III secretion system of *Pseudomonas aeruginosa* in Topics in Current Genetics, Vol. 11, Springer-Verlag Berlin, 2005. Mutations or deletions of the *P. aeruginosa* protein ExoU, are characteristic of non-cytotoxic *P. aeruginosa* strains, see for example Finck-Barbancon V, et al., Mol Microbiol. 1997; 25:547-557.

According to further aspects of the present invention, the subject has or is susceptible to *Pseudomonas aeruginosa*-mediated vaginosis and/or *Pseudomonas aeruginosa* infection secondary to cystic fibrosis.

Compositions are provided according to aspects of the present invention which include glycyrrhizin, or a pharmaceutically acceptable salt, hydrate, solvate, ester, amide, isomer or derivative thereof characterized by anti-*Pseudomonas aeruginosa* activity; and a pharmaceutically acceptable carrier, wherein the composition is formulated for topical administration to the cornea.

Combination Treatments

Combinations of therapeutic agents are administered according to aspects of the present invention to treat a bacterial infection of the cornea prophylactically or therapeutically.

In some aspects, glycyrrhizin and at least one additional therapeutic agent are administered to a subject to treat a bacterial infection in a subject in need thereof.

According to particular aspects, glycyrrhizin, or a pharmaceutically acceptable salt, hydrate, solvate, ester, amide, isomer or derivative thereof characterized by anti-*Pseudomonas aeruginosa* activity, and at least one additional therapeutic agent are administered to a subject to treat a *Pseudomonas aeruginosa* infection of the cornea, i.e. *Pseudomonas aeruginosa*-mediated keratitis, prophylactically or therapeutically, in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present invention include, but are not limited to, antibiotics, antivirals, analgesics, antipyretics, anti-inflammatory agents, non-steroidal anti-inflammatory agents and steroids.

Examples of antibiotics that can be administered in combination with glycyrrhizin according to aspects of the present invention include, but are not limited to, a carbapenem, a cephalosporin, a macrolide, a sulfonamide, a fluoroquinolone, a penicillin and a tetracycline.

Examples of particular antibiotics that can be administered in combination with glycyrrhizin according to aspects of the present invention include, but are not limited to, alatrofloxacin mesylate; amoxicillin; ampicillin; atovaquone azithromycin; aztreonam; carbenicillin; cefotetan; cefoxitin; cefazolin; cefaclor; ceftibuten; ceftizoxime; cefoperazone; cefuroxime; cefuroxime axetil; cefprozil; ceftazidime; cefotaxime; cefadroxil; ceftazidime; cephalexin; cefamandole nafate; cefepime; cefdinir; ceftriaxone; cefixime; cefpodoxime proxetil; chlortetracycline; cilastatin; ciprofloxacin; clarithromycin; clindamycin; clindamycin; colistimethate; dalfopristin; dapsone; demeclocycline; dirithromycin; doxycycline; erythromycin; gatifloxacin; imipenem; levofloxacins; loracarbef; lincomycin; meropenem; metronidazole; minocycline; moxifloxacin; neomycin; norfloxacin; ofloxacin; oxytetracycline; penicillin; piperacillin; polymyxin B; quinupristin; sulbactam; sulfamethoxazole; sulfisoxazole; rifabutin; linezolide; sulfacetamide; streptomycin; tetracycline; ticarcillin; trimethoprim; trovafloxacin mesylate; tobramycin; and vancomycin.

Combination therapies utilizing glycyrrhizin, or a pharmaceutically acceptable salt, hydrate, solvate, ester, amide, isomer or derivative thereof characterized by anti-*Pseudomonas aeruginosa* activity, and one or more additional therapeutic agents may show synergistic effects, e.g., a greater therapeutic effect than would be observed using glycyrrhizin, or a pharmaceutically acceptable salt, hydrate, solvate, ester, amide, isomer or derivative thereof characterized by anti-*Pseudomonas aeruginosa* activity, or the one or more additional therapeutic agents alone as a monotherapy.

According to aspects, combination therapies include: (1) pharmaceutical compositions that include glycyrrhizin, or a pharmaceutically acceptable salt, hydrate, solvate, ester, amide, isomer or derivative thereof characterized by anti-*Pseudomonas aeruginosa* activity, in combination with one or more additional therapeutic agents; and (2) co-administration of glycyrrhizin, or a pharmaceutically acceptable salt, hydrate, solvate, ester, amide, isomer or derivative thereof characterized by anti-*Pseudomonas aeruginosa* activity, with one or more additional therapeutic agents wherein glycyrrhizin, or a pharmaceutically acceptable salt, hydrate, solvate, ester, amide, isomer or derivative thereof characterized by anti-*Pseudomonas aeruginosa* activity, and the one or more additional therapeutic agents have not been formulated in the same composition. When using separate formulations, the glycyrrhizin, or a pharmaceutically acceptable salt, hydrate, solvate, ester, amide, isomer or derivative thereof characterized by anti-*Pseudomonas aeruginosa* activity, may be administered at the same time, intermittent times, staggered times, prior to, subsequent to, or combinations thereof, with reference to the administration of the one or more additional therapeutic agents.

Combination treatments can allow for reduced effective dosage and increased therapeutic index of glycyrrhizin, or a pharmaceutically acceptable salt, hydrate, solvate, ester, amide, isomer or derivative thereof characterized by anti-*Pseudomonas aeruginosa* activity, and the one or more additional therapeutic agents used in methods of the present invention.

According to aspects of the present invention, methods of treating bacterial infection of the cornea prophylactically or therapeutically in a subject, includes administration of glycyrrhizin, or a pharmaceutically acceptable salt, hydrate, solvate, ester, amide, isomer or derivative thereof characterized by anti-*Pseudomonas aeruginosa* activity, to the subject in combination with one or more antibiotics.

According to aspects of the present invention, methods of treating a *Pseudomonas aeruginosa*-mediated keratitis prophylactically or therapeutically in a subject, includes administration of glycyrrhizin, or a pharmaceutically acceptable salt, hydrate, solvate, ester, amide, isomer or derivative thereof characterized by anti-*Pseudomonas aeruginosa* activity, to the subject in combination with one or more antibiotics.

Methods of treating a bacterial infection prophylactically or therapeutically in a subject, are provided according to aspects of the present invention which include administering a combination of: an effective dose of glycyrrhizin, or a pharmaceutically acceptable salt, hydrate, solvate, ester, amide, isomer or derivative thereof characterized by anti-bacterial activity; and an effective dose of thrombomodulin, such as recombinant thrombomodulin, to the subject, thereby treating the bacterial infection prophylactically or therapeutically in the subject.

The effective dose of glycyrrhizin, or a pharmaceutically acceptable salt, hydrate, solvate, ester, amide, isomer or derivative thereof characterized by anti-bacterial activity; and the effective dose of recombinant thrombomodulin may be administered together or separately.

Thrombomodulin, such as recombinant human thrombomodulin, can be obtained commercially, isolated from natural sources, or synthesized by chemical or standard recombinant techniques of molecular biology.

For separate administration, the effective dose of glycyrrhizin, or a pharmaceutically acceptable salt, hydrate, solvate, ester, amide, isomer or derivative thereof characterized by anti-bacterial activity; and the effective dose of recombinant thrombomodulin may be administered by the same route or different routes of administration.

Glycyrrhizin, or a pharmaceutically acceptable salt, hydrate, solvate, ester, amide, isomer or derivative thereof characterized by anti-bacterial activity may be obtained commercially, isolated from natural sources or synthesized.

Recombinant thrombomodulin may be obtained commercially or synthesized.

Methods of treating a *Pseudomonas aeruginosa* infection prophylactically or therapeutically in a subject, are provided according to aspects of the present invention which include administering a combination of: an effective dose of glycyrrhizin, or a pharmaceutically acceptable salt, hydrate, solvate, ester, amide, isomer or derivative thereof characterized by anti-*Pseudomonas aeruginosa* activity; and an effective dose of recombinant thrombomodulin, to the subject, thereby treating the *Pseudomonas aeruginosa* infection prophylactically or therapeutically in the subject.

Methods of treating a *Pseudomonas aeruginosa* infection prophylactically or therapeutically in a subject, are provided according to aspects of the present invention which include administering a combination of: an effective dose of glycyrrhizin, or a pharmaceutically acceptable salt, hydrate, solvate, ester, amide, isomer or derivative thereof characterized by anti-*Pseudomonas aeruginosa* activity; and an effective dose of recombinant thrombomodulin, to the subject, wherein the subject has or is susceptible to *Pseudomonas aeruginosa*-mediated keratitis, *Pseudomonas aeruginosa*-mediated vaginosis and/or *Pseudomonas aeruginosa* infection secondary to cystic fibrosis, thereby treating or preventing *Pseudomonas aeruginosa* infection in the subject.

According to aspects of the present invention, the subject has or is susceptible to *Pseudomonas aeruginosa*-mediated keratitis and administering the effective dose of glycyrrhizin, or a pharmaceutically acceptable salt, hydrate, solvate, ester, amide, isomer or derivative thereof characterized by anti-*Pseudomonas aeruginosa* activity, includes topical administration of glycyrrhizin, or a pharmaceutically acceptable salt, hydrate, solvate, ester, amide, isomer or derivative thereof characterized by anti-*Pseudomonas aeruginosa* activity, to the cornea and administering the effective dose of recombinant thrombomodulin includes topical administration of the recombinant thrombomodulin to the cornea.

According to aspects of the present invention, the subject has or is susceptible to *Pseudomonas aeruginosa*-mediated keratitis and administering the effective dose of glycyrrhizin, or a pharmaceutically acceptable salt, hydrate, solvate, ester, amide, isomer or derivative thereof characterized by anti-*Pseudomonas aeruginosa* activity, includes subconjunctival administration of glycyrrhizin, or a pharmaceutically acceptable salt, hydrate, solvate, ester, amide, isomer or derivative thereof characterized by anti-*Pseudomonas aeruginosa* activity, and recombinant thrombomodulin.

According to aspects of the present invention, administering the effective dose of glycyrrhizin, or a pharmaceutically acceptable salt, hydrate, solvate, ester, amide, isomer or derivative thereof characterized by anti-*Pseudomonas aeruginosa* activity, includes systemic administration, such as intravenous administration, of glycyrrhizin and recombinant thrombomodulin.

According to aspects of the present invention, administering the effective dose of glycyrrhizin, or a pharmaceutically acceptable salt, hydrate, solvate, ester, amide, isomer or derivative thereof characterized by anti-*Pseudomonas aeruginosa* activity, includes parenteral administration of glycyrrhizin and recombinant thrombomodulin.

Methods of treating a bacterial infection prophylactically or therapeutically in a subject, are provided according to aspects of the present invention which include administering: an effective dose of glycyrrhizin, or a pharmaceutically acceptable salt, hydrate, solvate, ester, amide, isomer or derivative thereof characterized by anti-bacterial activity, and an effective dose of recombinant thrombomodulin to the subject, wherein the bacterial infection is or includes infection with a cytotoxic strain, non-cytotoxic strain or a mixture of cytotoxic and non-cytotoxic strains of bacteria.

Methods of treating a *Pseudomonas aeruginosa* infection prophylactically or therapeutically in a subject, are provided according to aspects of the present invention which include administering: an effective dose of glycyrrhizin, or a pharmaceutically acceptable salt, hydrate, solvate, ester, amide, isomer or derivative thereof characterized by anti-*Pseudomonas aeruginosa* activity, and an effective dose of recombinant thrombomodulin, to the subject, wherein the *Pseudomonas aeruginosa* infection is or includes infection with a cytotoxic strain, non-cytotoxic strain or a mixture of cytotoxic and non-cytotoxic strains of *Pseudomonas aeruginosa*.

The term "pharmaceutically acceptable salt" refers to salts which are suitable for use in a subject without undue toxicity or irritation to the subject and which are effective for their intended use.

Pharmaceutically acceptable salts include pharmaceutically acceptable acid addition salts and base addition salts. Pharmaceutically acceptable salts are well-known in the art, such as those detailed in S. M. Berge et al., J. Pharm. Sci., 66:1-19, 1977. Exemplary pharmaceutically acceptable salts are those suitable for use in a subject without undue toxicity or irritation to the subject and which are effective for their intended use which are formed with inorganic acids such as hydrochloric acid, hydrobromic acid, hydroiodic acid, nitric acid, phosphoric acid, sulfuric acid and sulfamic acid; organic acids such as acetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, formic acid, fumaric acid, glutamic acid, glycolic acid, glycerophosphoric acid, hemisulfic acid, heptanoic acid, hexanoic acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, trichloroacetic acid, trifluoroacetic acid and undecanoic acid; inorganic bases such as ammonia, hydroxide, carbonate, and bicarbonate of ammonium; organic bases such as Primary, secondary, tertiary and quaternary amine compounds ammonium, arginine, betaine, choline, caffeine, diolamine, diethylamine, diethanolamine, 2-dimethylaminoethanol, 2-diethylaminoethanol, dicyclohexylamine, dicyclohexylamine, dibenzylamine, N, N-dibenzylphenethylamine, 1-ephenamine, N,N'-dibenzylethylenediamine, ethanolamine, ethylamine, ethylenediamine, glucosamine, histidine, hydrabamine, isopropylamine, 1h-imidazole, lysine, methylamine, N-ethylpiperidine, N-methylpiperidine, N-methylmorpholine, N, N-dimethylaniline, piperazine, trolamine, methylglucamine, purines, piperidine, pyridine, theobromine, tetramethylammonium compounds, tetraethylammonium compounds, trimethylamine, triethylamine, tripropylamine and tributylamine and metal cations such as aluminum, calcium, copper, iron, lithium, magnesium, manganese, potassium, sodium, and zinc.

Subjects for treatment of infection prophylactically or therapeutically are identified using well-known medical and diagnostic techniques. In particular, a subject is identified as at risk of corneal infection, particularly by *Pseudomonas aeruginosa*, when any one or more risk factors is present, including use of extended wear contact lenses, ocular surface disease, ocular surgery, immunosuppression, employment in an environment known to increase likelihood of contact between the cornea and soil, such as agricultural workers, and recent or likely traumatic ocular surface events.

An effective dose is an amount which achieves a beneficial therapeutic effect.

As shown herein, the Minimum Inhibitory Concentration 50 ($MIC_{50}$) of glycyrrhizin on *Pseudomonas aeruginosa* cytotoxic and non-cytotoxic strains is 20 milligrams/milliliter. Effective doses can be determined for particular treatments without undue experimentation.

For glycyrrhizin, or a pharmaceutically acceptable salt, hydrate, solvate, ester, amide, isomer or derivative thereof characterized by anti-*Pseudomonas aeruginosa* activity, an effective dose is typically in the range of about 0.05 microgram to 1 milligram, such as, 0.075 to 500 micrograms, or such as 0.1 to 100 micrograms, administered 1-5/times per day, although more or less can be administered more or less frequently depending on the clinical requirements. For recombinant thrombomodulin, an effective dose is typically in the range of about 0.05 microgram to 1 milligram, such as, 0.075 to 500 micrograms, or such as 0.1 to 100 micrograms, administered 1-5/times per day, although more or less can be administered more or less frequently depending on the clinical requirements.

Methods for treating *Pseudomonas aeruginosa* infections of the cornea prophylactically include administration of a therapeutically effective amount of glycyrrhizin, or a pharmaceutically acceptable salt, hydrate, solvate, ester, amide, isomer or derivative thereof characterized by anti-*Pseudomonas aeruginosa* activity, prior to infection by *Pseudomonas aeruginosa* according to aspects of the present invention. For example, a therapeutically effective amount of glycyrrhizin is administered regularly for prophylactic effect, such as 0.05 microgram to 1 milligram, 0.075 to 500 micrograms, or 0.1 to 100 micrograms, administered 1-5/times per day, such as 0.05 microgram to 1 milligram, 0.075 to 500 micrograms, or 0.1 to 100 micrograms, administered 1-5/times every other day or such as 0.05 microgram to 1 milligram, 0.075 to 500 micrograms, or 0.1 to 100 micrograms, 1-5/times per week, although more or less can be administered more or less frequently depending on the clinical requirements.

Methods for treating *Pseudomonas aeruginosa* infections of the cornea prophylactically include administration of a therapeutically effective amount of glycyrrhizin, or a pharmaceutically acceptable salt, hydrate, solvate, ester, amide, isomer or derivative thereof characterized by anti-*Pseudomonas aeruginosa* activity, administered topically to the cornea regularly for prophylactic effect, such as 0.05 microgram to 1 milligram, 0.075 to 500 micrograms, or 0.1 to 100 micrograms, administered 1-5/times per day, such as 0.05 microgram to 1 milligram, 0.075 to 500 micrograms, or 0.1 to 100 micrograms, administered 1-5/times every other day or such as 0.05 microgram to 1 milligram, 0.075 to 500 micrograms, or 0.1 to 100 micrograms, administered 1-5/times per week, although more or less can be administered more or less frequently depending on the clinical requirements.

Methods for treating *Pseudomonas aeruginosa* infections of the cornea prophylactically or therapeutically include administration of a therapeutically effective amount of glycyrrhizin, or a pharmaceutically acceptable salt, hydrate, solvate, ester, amide, isomer or derivative thereof characterized by anti-*Pseudomonas aeruginosa* activity, administered topically to the cornea regularly for prophylactic and/or therapeutic effect, such as 0.05 microgram to 1 milligram, 0.075 to 500 micrograms, or 0.1 to 100 micrograms, administered 1-5/times per day, such as 0.05 microgram to 1 milligram, 0.075 to 500 micrograms, or 0.1 to 100 micrograms, administered 1-5/times every other day or such as 0.05 microgram to 1 milligram, 0.075 to 500 micrograms, or 0.1 to 100 micrograms, administered 1-5/times per week, although more or less can be administered more or less frequently depending on the clinical requirements, when any one or more risk factors is present, including use of extended wear contact lenses, ocular surface disease, ocular surgery, immunosuppression, employment in an environment known to increase likelihood of contact between the cornea and soil, such as agricultural workers, and recent or likely traumatic ocular surface events.

Methods for treating *Pseudomonas aeruginosa* infections of the cornea prophylactically or therapeutically include administration of a therapeutically effective amount of glycyrrhizin, or a pharmaceutically acceptable salt, hydrate, solvate, ester, amide, isomer or derivative thereof characterized by anti-*Pseudomonas aeruginosa* activity, administered topically to the eye within six to 24 hours, preferably 6 to 8 hours, following a traumatic ocular surface event.

Methods for treating *Pseudomonas aeruginosa* infections of the cornea prophylactically or therapeutically include administration of a therapeutically effective amount of glycyrrhizin, or a pharmaceutically acceptable salt, hydrate, solvate, ester, amide, isomer or derivative thereof characterized by anti-*Pseudomonas aeruginosa* activity, administered subconjunctivally to the eye within six to 24 hours, preferably 6 to 8 hours, following a traumatic ocular surface event.

Methods for treating *Pseudomonas aeruginosa* infections of the cornea prophylactically or therapeutically include administration of a therapeutically effective amount of glycyrrhizin, or a pharmaceutically acceptable salt, hydrate, solvate, ester, amide, isomer or derivative thereof characterized by anti-*Pseudomonas aeruginosa* activity, administered intravenously within six to 24 hours, preferably 6 to 8 hours, following a traumatic ocular surface event.

Methods for treating *Pseudomonas aeruginosa* infections of the cornea prophylactically or therapeutically include administration of a therapeutically effective amount of glycyrrhizin, or a pharmaceutically acceptable salt, hydrate, solvate, ester, amide, isomer or derivative thereof characterized by anti-*Pseudomonas aeruginosa* activity, administered subconjunctivally and topically to the cornea within six to 24 hours, preferably 6 to 8 hours, following a traumatic ocular surface event.

Methods for treating *Pseudomonas aeruginosa* infections of the cornea prophylactically or therapeutically include administration of a therapeutically effective amount of glycyrrhizin, or a pharmaceutically acceptable salt, hydrate, solvate, ester, amide, isomer or derivative thereof characterized by anti-*Pseudomonas aeruginosa* activity, administered subconjunctivally to the eye and intravenously within six to 24 hours, preferably 6 to 8 hours, following a traumatic ocular surface event.

Methods for treating *Pseudomonas aeruginosa* infections of the cornea prophylactically or therapeutically include administration of a therapeutically effective amount of glycyrrhizin, or a pharmaceutically acceptable salt, hydrate, solvate, ester, amide, isomer or derivative thereof characterized by anti-*Pseudomonas aeruginosa* activity, administered topically to the cornea and intravenously within six to 24 hours, preferably 6 to 8 hours, following a traumatic ocular surface event Methods for treating *Pseudomonas aeruginosa* infections of the cornea prophylactically or therapeutically include administration of a therapeutically effective amount, such as 0.05 microgram to 1 milligram, 0.075 to 500 micrograms, or 0.1 to 100 micrograms, of glycyrrhizin, or a pharmaceutically acceptable salt, hydrate, solvate, ester, amide, isomer or derivative thereof characterized by anti-*Pseudomonas aeruginosa* activity, administered topically and/or subconjunctivally to the cornea and/or intravenously within six to 24 hours, preferably 6 to 8 hours, following a traumatic ocular surface event.

The term "subject" refers to an individual having or susceptible to having a bacterial infection, such as *Pseudomonas aeruginosa*. The subject is typically a mammalian or avian subject such as, but not limited to, a human, non-human primate, cow, horse, dog, cat, sheep, pig, mouse, rat, guinea pig or poultry. According to aspects of methods of the present invention, the subject is human. According to aspects of methods of the present invention, the subject is a horse.

Compositions are provided according to aspects of the present invention which include glycyrrhizin, or a pharmaceutically acceptable salt, hydrate, solvate, ester, amide, isomer or derivative thereof characterized by anti-*Pseudomonas aeruginosa* activity; and a pharmaceutically acceptable carrier, wherein the composition is formulated for topical administration to the cornea.

Compositions are provided according to aspects of the present invention which include glycyrrhizin, or a pharmaceutically acceptable salt, hydrate, solvate, ester, amide, isomer or derivative thereof characterized by anti-*Pseudomonas aeruginosa* activity; one or more additional therapeutic agents; and a pharmaceutically acceptable carrier, wherein the composition is formulated for administration to the cornea, via systemic or local route of administration.

Compositions are provided according to aspects of the present invention which include glycyrrhizin, or a pharmaceutically acceptable salt, hydrate, solvate, ester, amide, isomer or derivative thereof characterized by anti-*Pseudomonas aeruginosa* activity; one or more antibiotics; and a pharmaceutically acceptable carrier, wherein the composition is formulated for administration to the cornea, via systemic or local route of administration.

Compositions are provided according to aspects of the present invention which include glycyrrhizin, or a pharmaceutically acceptable salt, hydrate, solvate, ester, amide, isomer or derivative thereof characterized by anti-*Pseudomonas aeruginosa* activity; recombinant thrombomodulin; and a pharmaceutically acceptable carrier, wherein the composition is formulated for administration to the cornea, via systemic or local route of administration.

A pharmaceutical composition according to the invention generally includes about 0.1-99% of glycyrrhizin, a pharmaceutically acceptable salt, hydrate, solvate, ester, amide, isomer or derivative thereof.

A pharmaceutical composition according to the invention generally includes about 0.1-99% of glycyrrhizin, a pharmaceutically acceptable salt, hydrate, solvate, ester, amide, isomer or derivative thereof; and 0.1-99% of one or more additional therapeutic agents.

A pharmaceutical composition according to the invention generally includes about 0.1-99% of glycyrrhizin, a pharmaceutically acceptable salt, hydrate, solvate, ester, amide, isomer or derivative thereof; and 0.1-99% of one or more antibiotics.

A pharmaceutical composition according to the invention generally includes about 0.1-99% of glycyrrhizin, a pharmaceutically acceptable salt, hydrate, solvate, ester, amide, isomer or derivative thereof; and 0.1-99% of thrombomodulin.

Pharmaceutical compositions suitable for delivery to a subject may be prepared in various forms illustratively including physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral, systemic or local administration, such as, but not limited to, systemic or local injection. According to particular aspects of the present invention, administration is by systemic administration, particularly intravenous injection. According to particular aspects of the present invention, administration is by local administration, particularly subconjunctival injection. According to particular aspects of the present invention, administration is by local administration, particularly topical application to the cornea.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

In particular aspects, glycyrrhizin, or a pharmaceutically acceptable salt, hydrate, solvate, ester, amide, isomer or derivative thereof characterized by anti-bacterial activity, such as anti-*Pseudomonas aeruginosa* activity, is formulated for topical application to the cornea.

A topical formulation for administration to the cornea locally can be, but is not limited to, an eyedrop, sprays, ointment, or gel in particular aspects. Topical dosage forms such as eyedrops, sprays, ointment, or gel bases are described in Remington: The Science and Practice of Pharmacy, 21$^{st}$ Ed., Lippincott Williams & Wilkins, 2006, pp. 850-888, such as p. 880-882 and p. 886-888; and in Allen, L. V. et al., Ansel's Pharmaceutical Dosage Forms and Drug Delivery Systems, 8$^{th}$ Ed., Lippincott Williams & Wilkins, 2005, p. 277-297.

Subconjunctival or topical administration to the cornea can be administration to one or both corneas of a subject, as required to treat an infection prophylactically or therapeutically.

Glycyrrhizin, or a pharmaceutically acceptable salt, hydrate, solvate, ester, amide, isomer or derivative thereof characterized by anti-bacterial activity, particularly anti-*Pseudomonas aeruginosa* activity, with or without an additional therapeutic agent, can be delivered via any suitable method and/or device known in the art such as by injection, ocular implant, spray or eyedrop applicator, eye cup applicator, and ophthalmic dosing systems for delivery to the cornea. Ophthalmic preparations of may be formulated in any form suitable for delivery to the cornea such as, but not limited to, an injectable formulation, topical solution, gel or suspension. An ophthalmic implant, such as a pump or polymer including glycyrrhizin, or a pharmaceutically acceptable salt, hydrate, solvate, ester, amide, isomer or derivative thereof characterized by anti-bacterial activity, particularly anti-*Pseudomonas aeruginosa* activity, with or without an additional therapeutic agent, can be used. Optionally, glycyrrhizin, or a pharmaceutically acceptable salt, hydrate, solvate, ester, amide, isomer or derivative thereof characterized by anti-bacterial activity, particularly anti-*Pseudomonas aeruginosa* activity, with or without an additional therapeutic agent, can be delivered by implantation of a controlled release formulation which releases the glycyrrhizin, or a pharmaceutically acceptable salt, hydrate, solvate, ester, amide, isomer or derivative thereof characterized by anti-bacterial activity, particularly anti-*Pseudomonas aeruginosa* activity, with or without an additional therapeutic agent, at a determined rate.

Ophthalmic formulations including glycyrrhizin, or a pharmaceutically acceptable salt, hydrate, solvate, ester, amide, isomer or derivative thereof characterized by anti-bacterial activity, particularly anti-*Pseudomonas aeruginosa* activity, with or without an additional therapeutic agent, can include ingredients such as, but not limited to, a diluent, solvent, suspending fluid, preservative, a buffer and a thickening agent.

Pharmaceutically acceptable carriers and formulation of pharmaceutical compositions are known in the art, illustratively including, but not limited to, as described in Remington: The Science and Practice of Pharmacy, 21$^{st}$ Ed., Lippincott, Williams & Wilkins, Philadelphia, Pa., 2006; and Allen, L. V. et al., Ansel's Pharmaceutical Dosage Forms and Drug Delivery Systems, 8$^{th}$ Ed., Lippincott, Williams & Wilkins, Philadelphia, Pa., 2005.

Embodiments of inventive compositions and methods are illustrated in the following examples. These examples are provided for illustrative purposes and are not considered limitations on the scope of inventive compositions and methods.

EXAMPLES

Example 1

Mice

Eight-week-old female C57BL/6 (B6) mice were purchased from the Jackson Laboratory (Bar Harbor, Me.).

Bacterial Culture and Infection

P. aeruginosa strains, KEI 1025, a non-cytotoxic clinical isolate strain expressing exoT and exoS, and not expressing exoU, described in Estrellas P S, Jr., et al., Curr Eye Res. 2000; 20:157-165 (obtained from Kresge Eye Institute, Detroit, Mich.), and a cytotoxic strain, 19660, expressing exoU, described in Finck-Barbancon V, et al., Mol Microbiol. 1997; 25:547-557; and Fleiszig S M, et al., Infect Immun. 1997; 65:579-586 (obtained from American Type Culture Collection, ATCC, Manassas, Va.), were grown in peptone tryptic soy broth (PTSB) medium in a rotary shaker water bath at 37° C. and 150 rpm for 18 h to an optical density (measured at 540 nm) between 1.3-1.8. Bacterial cultures were pelleted by centrifugation at 5,500 g for 10 min. Pellets were washed once with sterile saline, re-centrifuged, re-suspended and diluted in sterile saline. Anesthetized (using anhydrous ethyl ether) mice were placed beneath a stereoscopic microscope at 40× magnification. The left cornea was scarified with three 1-mm incisions using a sterile 25$^{5/8}$ gauge needle. The wounded corneal surface was topically treated with 5 µl containing 1×10$^7$ CFU/µl (KEI 1025) or 1×10$^6$ CFU/µl (ATCC strain 19660) of the P. aeruginosa suspension.

Ocular Response to Bacterial Infection

An established corneal disease grading scale, described in detail in Hazlett L D, et al., Invest Ophthalmol Vis Sci. 1987; 28:1978-1985, was used to assign a clinical score value to each infected eye at 1, 3 and 5 days post infection (p.i.). Clinical scores were designated as: 0=clear or slight opacity, partially or fully covering the pupil; +1=slight opacity, fully covering the anterior segment; +2=dense opacity, partially or fully covering the pupil; +3=dense opacity, covering the entire anterior segment; and +4=corneal perforation or phthisis. Clinical scores were used to statistically compare disease severity and were accompanied by photographs using a slit lamp (5 days p.i.) to confirm and illustrate the response.

GLY or CBX Treatment

The left eyes of B6 mice (n=5/group/time) were injected with 5 µl of 2 µg/µl glycyrrhizin (GLY) (Sigma-Aldrich, St. Louis, Mo.) or PBS (control) subconjunctivally, one day before infection. Similar treatment was done using carbenoxolone (CBX) (Sigma-Aldrich, St. Louis, Mo.). All mice were injected intraperitoneally (IP) at 1 and 3 days p.i. with 100 µl of GLY (2 µg/µl) or CBX (1 µg/µl). PBS served as control for all these experiments. In a separate similar experiment mice were treated one day before infection with GLY subconjunctivally and injected intraperitoneally (i.p.) with GLY plus recombinant (r) HMGB1 (1 µg/100 µl) or GLY plus PBS. IP injections were similarly given at 1 and 3 days p.i. In an additional experiment, KEI 1025 infected B6 mice were treated with 5 µl of 2 µg/µl GLY subconjunctivally at 6 hours p.i. and injected intraperitoneally at 1 and 3 days p.i. with 100 µl of GLY (2 µg/µl).

Real Time RT-PCR

KEI 1025 or ATCC strain 19660 infected GLY or PBS treated mice were sacrificed at 5 days p.i. and the normal, contralateral (uninfected) and infected cornea was harvested. For each cornea, total RNA was isolated (RNA STAT-60™; Tel-Test, Friendswood, Tex.) according to the manufacturer's instructions. Upon spectrophotometric quantification at 260 nm, 1 µg of each RNA sample was reverse transcribed using Moloney-murine leukemia virus (M-MLV) reverse transcriptase (Invitrogen, Carlsbad, Calif.) to produce a cDNA template for the PCR reaction. cDNA products were diluted 1:25 with diethylpyrocarbonate (DEPC)-treated water. A 2 µl aliquot of diluted cDNA was used for the real-time RT-PCR reaction with Real-Time SYBR® Green/Fluorescein PCR Master Mix (Bio-Rad) and primer concentrations of 10 µM (total 10 µl reaction volume). After a pre-programmed hot start cycle (3 min at 95° C.), the parameters used for PCR amplification were: 15 sec at 95° C. and 60 sec at 60° C. with the cycles repeated 45 times. Optimal conditions for PCR amplification of cDNA were established using routine methods. mRNA levels of HMGB1, RAGE, IL-1β, TLR2, TLR4, CXCL2, TNF-α, NLR family pyrin domain containing 3 (NLRP3), NLR family CARD domain containing 4 (NLRC4), IL-12, TGF-β, IL-10, single Ig IL-1-related receptor (SIGIRR) and interleukin 1 receptor-like 1 (ST2) were tested by real-time RT-PCR (CFX Connect™ Real-Time PCR Detection System; Bio-Rad, Richmond, Calif.). The fold differences in gene expression were calculated after normalization to β-actin and expressed as the relative mRNA concentration+SEM.

Enzyme-Linked Immunosorbent Assay (ELISA)

KEI 1025 or ATCC strain 19660 infected GLY or PBS treated, B6 mice (n=5/group/time) were sacrificed at 3 and 5 days p.i. and normal and infected corneas harvested. To quantify IL-1β and CXCL2 proteins, individual corneas were homogenized in 1 ml of 50 mM potassium phosphate buffer (pH 6.0) containing 0.5% HTAB (hexadecyltrimethylammonium bromide, Sigma). To quantify HMGB1, cathelicidin-related antimicrobial peptide (CRAMP), mouse beta defensin 2 (mBD2) and mouse beta defensin 3 (mBD3) protein levels, individual corneas were homogenized in 500 µl of PBS containing 0.1% Tween 20 (Sigma) and protease inhibitors (Roche, Indianapolis, Ind.). Corneal homogenates were centrifuged at 12,000 g for 10 min. A 50 µl aliquot of each supernatant was assayed in duplicate to quantify IL-1β, CXCL2, HMGB1 and mBD2 proteins. A 100 µl aliquot of CRAMP and mBD3 supernatant was assayed in duplicate to quantify corresponding protein levels. Undiluted supernatant aliquots were used to quantify all proteins except CXCL2 (1:2 dilution) and HMGB1 (1:5 dilution). An HMGB1 ELISA kit was purchased from Chondrex Inc., Redmond, Wash. CRAMP, mBD2 and mBD3 ELISA kits were purchased from MyBioSource, Inc., San Diego, Calif. All other ELISA kits were purchased from R&D Systems, Minneapolis, Minn. Assays were run following the manufacturer's instructions. Sensitivities of the assays were: 2.31 µg/ml (IL-1β), 1.5 µg/ml (CXCL2), 0.8 ng/ml (HMGB1), 0.39 µg/ml (CRAMP), 2 µg/ml (mBD2) and 12 µg/ml (mBD3).

Myeloperoxidase (MPO) Assay

This assay was used to quantitate neutrophils in the cornea of GLY and PBS treated mice (n=5/group/time) infected with KEI 1025 or ATCC strain 19660. Individual corneas were removed at 3 and 5 days p.i. and homogenized in 1.0 ml of 50 mM phosphate buffer (pH 6.0) containing 0.5% HTAB. Samples were freeze-thawed four times and after centrifugation, 100 µl of the supernatant was added to 2.9 ml of 50 mM phosphate buffer containing o-dianisidine dihydrochloride (16.7 mg/ml, Sigma) and hydrogen peroxide (0.0005%). The change in absorbency was monitored at 460 nm for 5 min at 30 sec intervals. The slope of the line was determined for each sample and used to calculate units of MPO/cornea. One unit of MPO activity is equivalent to $\sim 2 \times 10^5$ neutrophils.

Quantification of Viable Bacteria

Mice were sacrificed at 3 and 5 days p.i. and KEI 1025 or ATCC strain 19660 infected corneas from GLY, CBX or PBS (or GLY+/−rHMGB1) treated B6 mice were harvested (n=5/group/time). Each cornea was homogenized in 1 ml of sterile saline (0.85% NaCl, pH 7.4) containing 0.25% BSA. A 100 µl of the corneal homogenate was serially diluted (1:10) in sterile saline containing 0.25% BSA. Selected dilutions were plated in triplicate on selective culture medium (Difco™ Pseudomonas Isolation Agar, BD Biosciences, Inc., Franklin Lakes, N.J.). Plates were incubated overnight at 37° C. and viable bacteria manually counted. Results are reported as $\log_{10}$ CFU/cornea±SEM.

Histopathology

Whole eyes infected with KEI 1025 (n=3/group/time) were enucleated from GLY or PBS treated B6 mice at 3 and 5 days p.i. Eyes were immersed in PBS, rinsed, and fixed in 1% osmium tetroxide, 2.5% glutaraldehyde, and 0.2 M Sorenson's phosphate buffer (pH 7.4) (1:1:1) at 4° C. for 3 h. Eyes were rinsed with 0.1 M phosphate buffer, dehydrated in graded ethanols and propylene oxide, and then infiltrated and embedded in Epon-araldite. Thick sections (1.5 µm) were cut, stained with Richardson's stain, observed, and photographed (Leica DM4000B, Leica Microsystems, Inc.).

Bacterial Growth and Minimum Inhibitory Concentration (MIC)

Bacterial cultures (KEI 1025 and ATCC 19660) were prepared as described above and bacterial growth examined as described in Guerra C R, et al., Mem Inst Oswaldo Cruz. 2012; 107:582-590; and Franzblau S G, et al., Tuberculosis (Edinb). 2012; 92:453-488 with the following modifications. Serial dilutions of GLY were prepared in PTSB (0-40 mg/ml) in sterile tubes and 5 ml of each bacterial culture (washed and reconstituted in saline) was added. The MIC of GLY was determined by spectrophotometric reading at 540 nm following incubation at 37° C. for 18 h. $MIC_{50}$ and $MIC_{90}$ values were defined as the lowest GLY concentrations that resulted in a 50% and 90% decrease in absorbance compared to the growth control, respectively.

Statistical Analysis

The difference in clinical score between two groups was analyzed by the Mann-Whitney U test (GraphPad Prism, San Diego, Calif.). For comparisons of three or more groups (RT-PCR), a one-way ANOVA followed by the Bonferroni's multiple comparison test (GraphPad Prism) was used for analysis. For all other experiments in which two groups were compared (ELISA, MPO, plate count, RT-PCR, and MIC), an unpaired, two-tailed Student's I-test was used to determine significance. For each test, $p<0.05$ was considered significant and data are shown as mean+SEM. All experiments were repeated at least once to ensure reproducibility.

Results

Comparison of GLY and CBX Treatment after KEI 1025 Infection

FIGS. 1A-1F show disease response after infection with KEI 1025 and GLY or CBX treatment FIG. 1(A) shows that GLY treated mice exhibited significantly less corneal disease with lower clinical scores than PBS treated mice (n=10 mice/group/time), at 1, 3 and 5 days p.i. ($p<0.05$, $p<0.005$ and $p<0.05$). Photographs taken with a slit lamp of representative eyes from PBS (FIG. 1B) and GLY (FIG. 1C) treated mice at 5 days p.i illustrate the reduced opacity evident in the GLY vs PBS treated group. For the CBX treatment group (FIG. 1D), statistically significant reduction in disease scores was seen at 3 ($p<0.05$), but not at 5 ($p=0.2$) days p.i. Photographs taken with a slit lamp of representative eyes from PBS (FIG. 1E) and CBX (FIG. 1F) treated groups are shown at 5 days p.i.

Photographs taken with a slit lamp at 5 days p.i. from PBS (FIG. 1B) and GLY (FIG. 1C) or PBS (FIG. 1E) and CBX (FIG. 1F) treated mice confirmed reduced opacity, but GLY treated eyes appeared to have less infiltrate. Data were analyzed using a nonparametric Mann-Whitney U test. Horizontal lines indicate the median values. Magnification=8×; n=10/group/time.

Real Time RT-PCR: GLY/CBX Treatment after KEI 1025 Infection

FIGS. 2A-G and FIGS. 3A-G show results of real-time RT-PCR after infection with KEI 1025. In all of FIGS. 2A-2G and 3A-3G, the white bar shows result in PBS treated eye, darkest bar shows result of treatment with CBX and the gray bar shows the result of treatment with GLY. Data are mean+SEM analyzed using one-way ANOVA followed by the Bonferroni's multiple comparison test. n=10/group/time.

Figure 2C:
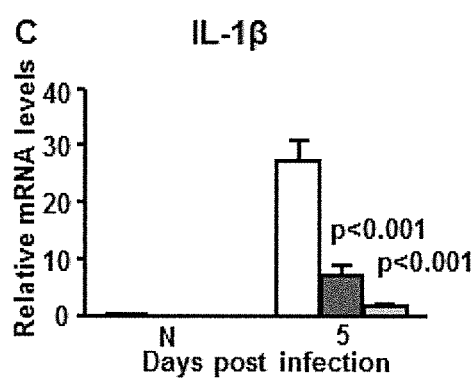
FIG. 2C is a graph showing relative IL-1 beta mRNA levels in cornea analyzed by real-time RT-PCR after infection of corneas with *Pseudomonas aeruginosa* and treatment with PBS, CBX or GLY.
Figure 2D:
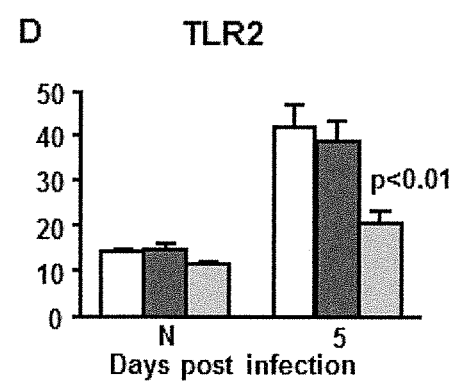
FIG. 2D is a graph showing relative TLR2 mRNA levels in cornea analyzed by real-time RT-PCR after infection of corneas with *Pseudomonas aeruginosa* and treatment with PBS, CBX or GLY.
Figure 2E:
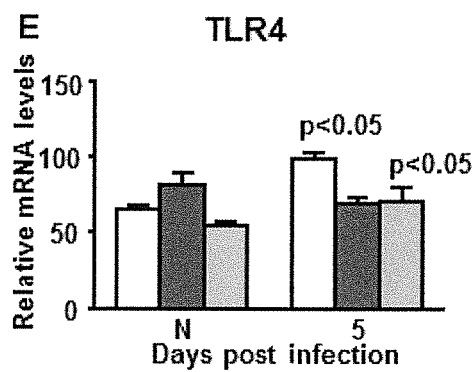
FIG. 2E is a graph showing relative TLR4 mRNA levels in cornea analyzed by real-time RT-PCR after infection of corneas with *Pseudomonas aeruginosa* and treatment with PBS, CBX or GLY.
Figure 2F:
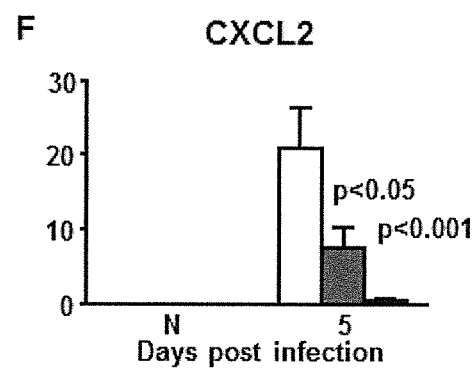
FIG. 2F is a graph showing relative CXCL2 mRNA levels in cornea analyzed by real-time RT-PCR after infection of corneas with *Pseudomonas aeruginosa* and treatment with PBS, CBX or GLY.
Figure 2G:
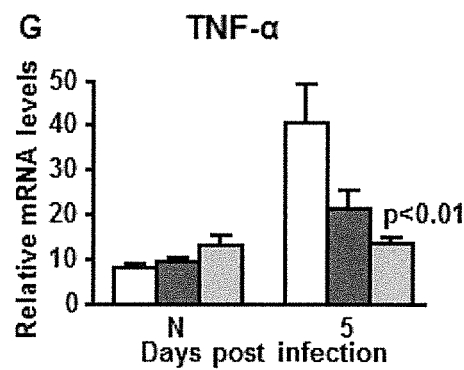
FIG. 2G is a graph showing relative TNF-alpha mRNA levels in cornea analyzed by real-time RT-PCR after infection of corneas with *Pseudomonas aeruginosa* and treatment with PBS, CBX or GLY.
Figure 3A:
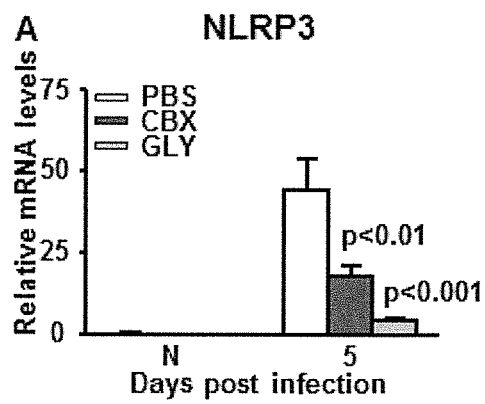
FIG. 3A is a graph showing relative NLRP3 mRNA levels in cornea analyzed by real-time RT-PCR after infection of corneas with *Pseudomonas aeruginosa* and treatment with PBS, CBX or GLY.
Figure 3B:
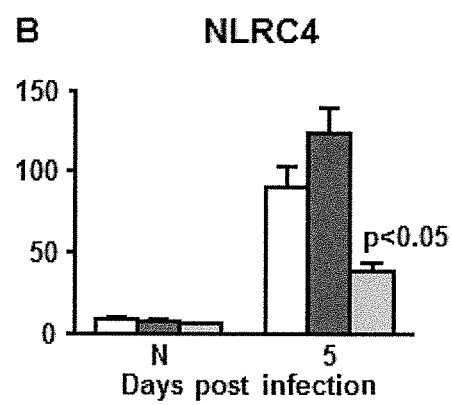
FIG. 3B is a graph showing relative NLRC4 mRNA levels in cornea analyzed by real-time RT-PCR after infection of corneas with *Pseudomonas aeruginosa* and treatment with PBS, CBX or GLY.
Figure 3C:
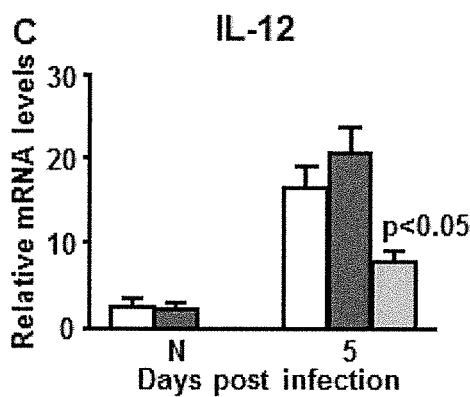
FIG. 3C is a graph showing relative IL-12 mRNA levels in cornea analyzed by real-time RT-PCR after infection of corneas with *Pseudomonas aeruginosa* and treatment with PBS, CBX or GLY.
Figure 3D:
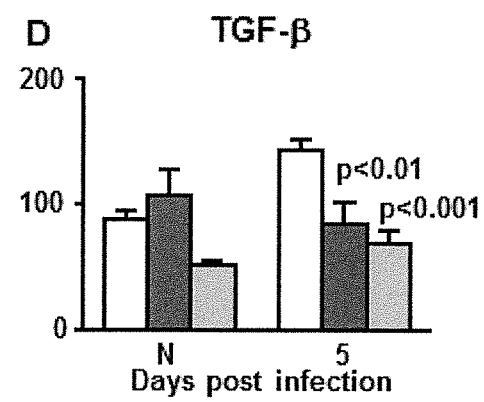
FIG. 3D is a graph showing relative TGF-beta mRNA levels in cornea analyzed by real-time RT-PCR after infection of corneas with *Pseudomonas aeruginosa* and treatment with PBS, CBX or GLY.
Figure 3E:
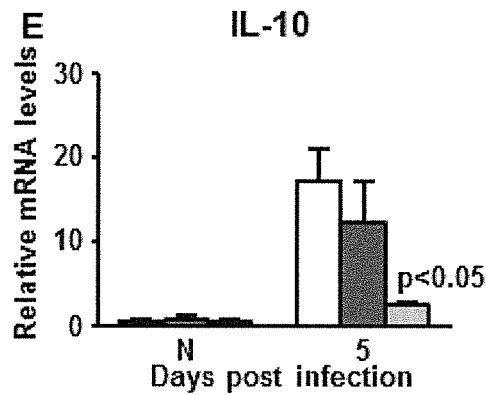
FIG. 3E is a graph showing relative IL-10 mRNA levels in cornea analyzed by real-time RT-PCR after infection of corneas with *Pseudomonas aeruginosa* and treatment with PBS, CBX or GLY.
Figure 3F:
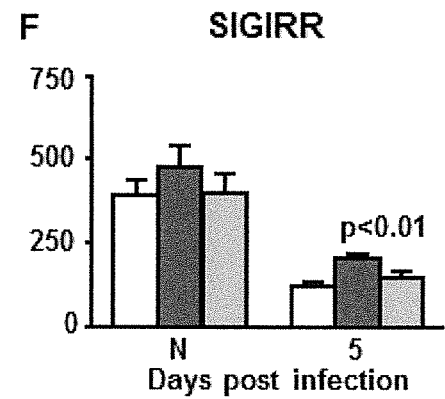
FIG. 3F is a graph showing relative SIGIRR mRNA levels in cornea analyzed by real-time RT-PCR after infection of corneas with *Pseudomonas aeruginosa* and treatment with PBS, CBX or GLY.
Figure 3G:
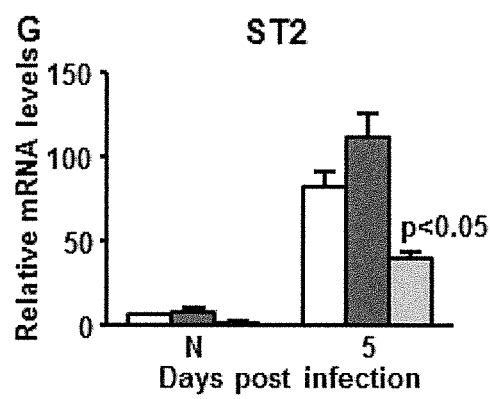
FIG. 3G is a graph showing relative ST2 mRNA levels in cornea analyzed by real-time RT-PCR after infection of corneas with *Pseudomonas aeruginosa* and treatment with PBS, CBX or GLY.

Focusing on 5 days p.i., GLY significantly reduced HMGB1 ($p<0.05$) while no difference was seen for CBX when compared with PBS treatment (FIG. 2A). GLY treatment reduced RAGE mRNA levels (FIG. 2B) when compared with PBS but not significantly. IL-1β mRNA levels were significantly reduced by GLY ($p<0.001$) and by CBX ($p<0.001$) when compared to PBS (FIG. 2C). GLY significantly reduced TLR2 ($p<0.01$), while CBX treatment did not differ from PBS controls (FIG. 2D). TLR4 mRNA was reduced by GLY ($p<0.05$) and CBX ($p<0.05$) similarly when compared to PBS (FIG. 2E). CXCL2 was reduced by GLY ($p<0.001$) and by CBX ($p<0.05$) when compared with PBS (FIG. 2F). TNF-α mRNA levels were reduced by both GLY and CBX, but only GLY ($p<0.01$) was significant compared with control levels (FIG. 2G). GLY and CBX also reduced mRNA levels for NLRP3 ($p<0.001$ and $p<0.01$), and for TGF-β ($p<0.001$ and $p<0.01$) (FIGS. 3A and 3D). However, only GLY reduced mRNA levels of NLRC4 ($p<0.05$) and IL-12 ($p<0.05$) compared with CBX or PBS treatment (FIGS. 3B and 3C). GLY also reduced anti-inflammatory molecules IL-10 ($p<0.05$, FIG. 3E), and ST2 ($p<0.05$, FIG. 3G), while CBX increased modestly SIGIRR mRNA levels ($p<0.01$, FIG. 3F). For all normal corneas, GLY significantly reduced mRNA levels only for RAGE (FIG. 2B, $p<0.05$), with no differences for the other molecules tested among the three groups (FIGS. 2 and 3).

ELISA, MPO, Histopathology and Plate Count

GLY treatment significantly decreased mRNA expression of HMGB1, and thus, its effects were studied further for effects on chemotactic cytokines, and neutrophilic infiltrate. For plate counts, GLY and CBX were comparatively tested.

Figure 4A:
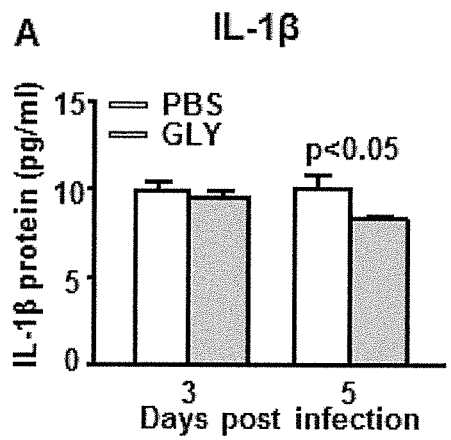
FIG. 4A is a graph showing IL-1 beta levels in cornea after infection of corneas with *Pseudomonas aeruginosa* and treatment with PBS (white bars) or GLY (gray bars)
Figure 4B:
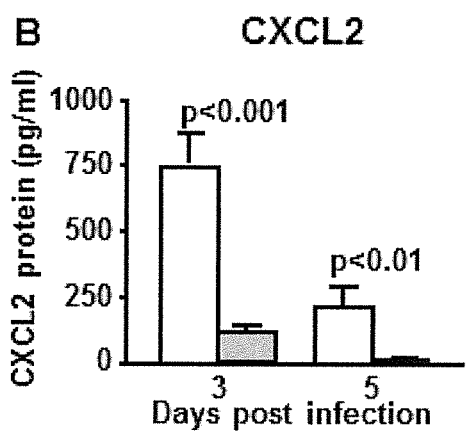
FIG. 4B is a graph showing CXCL2 levels in cornea after infection of corneas with *Pseudomonas aeruginosa* and treatment with PBS (white bars) or GLY (gray bars)
Figure 4C:
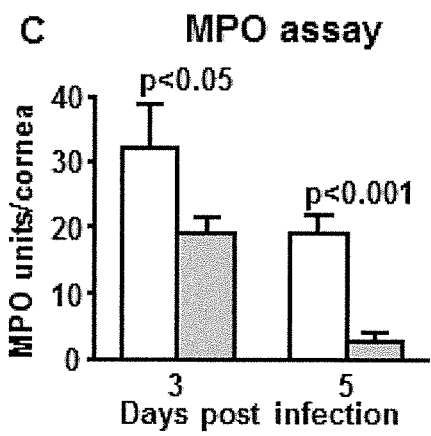
FIG. 4C is a graph showing the results of myeloperoxidase (MPO) assay in cornea after infection of corneas with *Pseudomonas aeruginosa* and treatment with PBS (white bars) or GLY (gray bars)

Treatment with GLY significantly decreased IL-1 protein at 5 days p.i. (FIG. 4A, p<0.05), but was no different from control values at 3 days p.i. CXCL2 protein expression was significantly decreased both at 3 (p<0.001) and 5 (p<0.01) days p.i. (FIG. 4B) in GLY vs. PBS treated cornea. Consistent with reduced levels of these neutrophil chemoattractant cytokines, an MPO assay (FIG. 4C) revealed decreased neutrophils in cornea at both 3 (p<0.05) and 5 (p<0.001) days p.i. (FIG. 4C). In all of FIGS. 4A-4C, the white bar shows result in PBS treated eye and the gray bar shows the result of treatment with GLY.

Figure 5A:
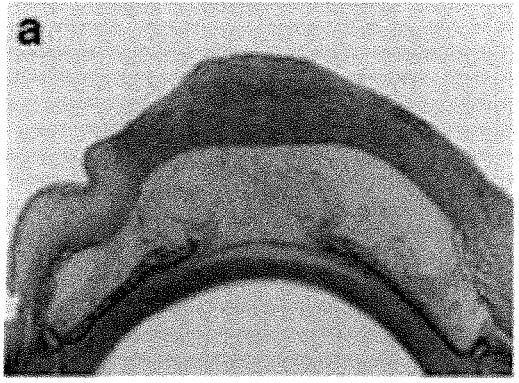
FIG. 5A is an image of a section (1.5 µm thick) of a PBS treated eye at 3 days p.i. where the cornea was infected with *Pseudomonas aeruginosa*, stained with Richardson's stain for histopathological analysis.
Figure 5B:
FIG. 5B is an image of a section (1.5 µm thick) of a GLY treated eye at 3 days p.i. where the cornea was infected with *Pseudomonas aeruginosa*, stained with Richardson's stain for histopathological analysis; reduced corneal destruction and infiltrate is seen in the GLY treated vs PBS (5A) treated eye.
Figure 5C:
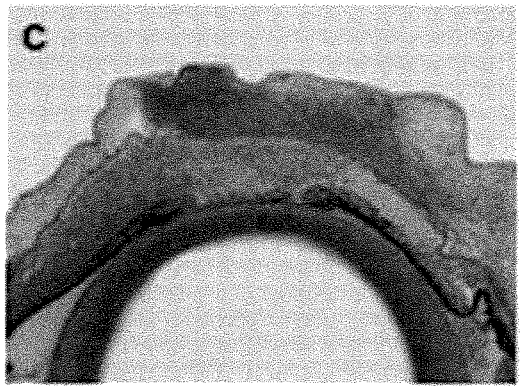
FIG. 5C is an image of a section (1.5 µm thick) of a PBS treated eye at 5 days p.i. where the cornea was infected with *Pseudomonas aeruginosa*, stained with Richardson's stain for histopathological analysis.
Figure 5D:
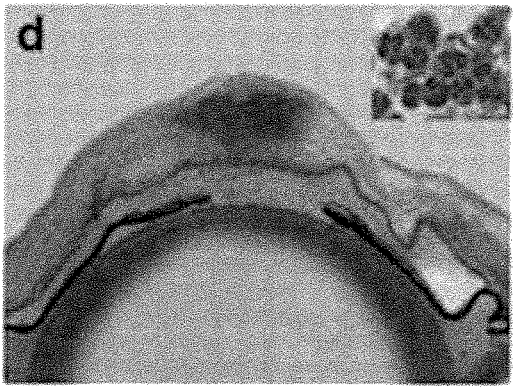
FIG. 5D is an image of a section (1.5 µm thick) of a GLY treated eye at 5 days p.i. where the cornea was infected with *Pseudomonas aeruginosa*, stained with Richardson's stain for histopathological analysis reduced damage to the cornea and a decreased cellular infiltrate is seen in the GLY treated vs PBS treated eye.

The KEI 1025 infected, GLY or PBS treated eyes also were examined histopathologically. Reflective of the MPO data, GLY treated eyes showed a markedly reduced cellular infiltrate (predominantly PMN, as illustrated in the inset in FIG. 5D) in the corneal stroma and anterior chamber both at 3 (FIG. 5B) and 5 days p.i. (FIG. 5D). In contrast, the PBS treated eyes showed a heavier cellular infiltrate in the corneal stroma, denudation of the corneal epithelium, stromal degradation and edema both at 3 and 5 days p.i. (FIGS. 5A and 5C, respectively). Magnification=30×; Inset=490×, n=3/group/time.

Figure 6A:
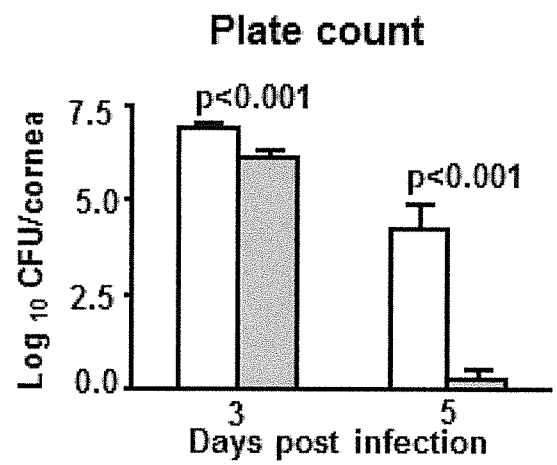
FIG. 6A is a graph showing the results of plate count showing bacterial load in the cornea after infection of corneas with *Pseudomonas aeruginosa* and treatment with PBS (white bars) or GLY (gray bars)
Figure 6B:
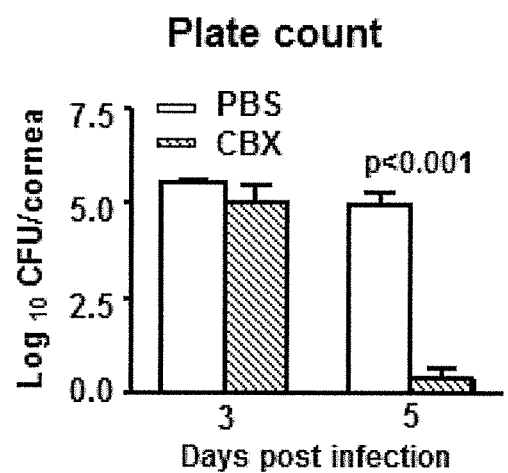
FIG. 6B is a graph showing the results of plate count showing bacterial load in the cornea after infection of corneas with *Pseudomonas aeruginosa* and treatment with PBS (white bars) or CBX (striped bars)

The bacterial load in the corneas of GLY treated mice was reduced at both 3 (p<0.001) and 5 (p<0.001) days p.i. (FIG. 6A). In FIG. 6A, the white bar shows result in PBS treated eye and the gray bar shows the result of treatment with GLY. After CBX treatment plate count was significantly reduced (p<0.001) only at 5 days p.i. (FIG. 6B) but not at 3 days p.i. as seen with GLY treatment. All data for FIGS. 4A-C, 5A-D and 6A-B are mean+SEM and were analyzed using a two-tailed Student t test (n=5/group/time).

GLY Reduces HMGB1 and Enhances Antimicrobial Peptides

Figure 7A:
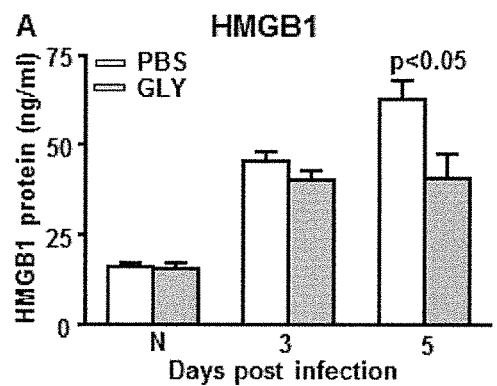
FIG. 7A is a graph showing HMGB1 levels in corneas after infection of the corneas with *Pseudomonas aeruginosa* and treatment with PBS (white bars) or GLY (gray bars)
Figure 7B:
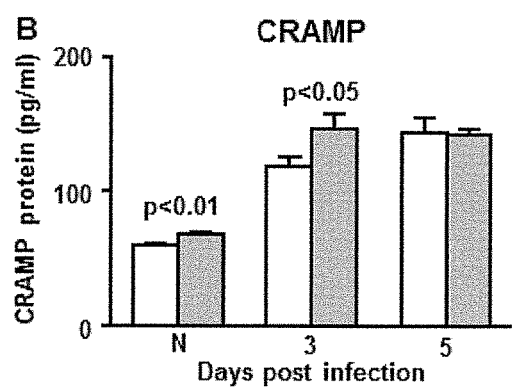
FIG. 7B is a graph showing CRAMP levels in corneas after infection of the corneas with *Pseudomonas aeruginosa* and treatment with PBS (white bars) or GLY (gray bars)
Figure 7C:
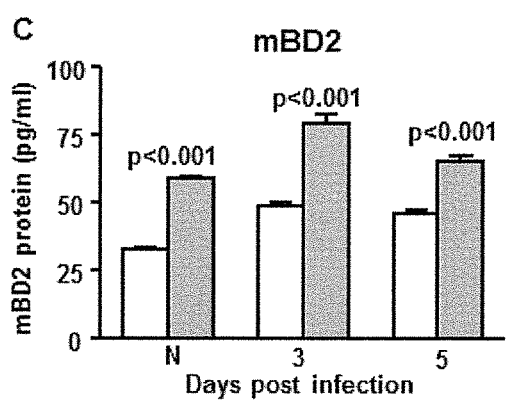
FIG. 7C is a graph showing mBD2 levels in corneas after infection of the corneas with *Pseudomonas aeruginosa* and treatment with PBS (white bars) or GLY (gray bars)
Figure 7D:
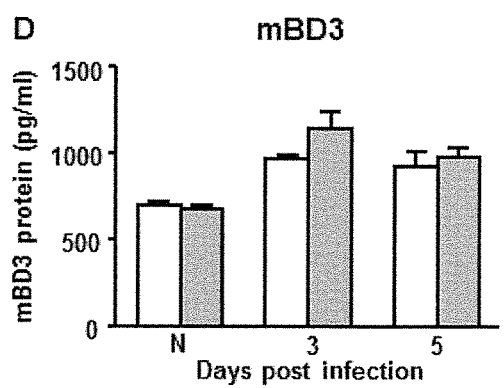
FIG. 7D is a graph showing mBD3 levels in corneas after infection of the corneas with *Pseudomonas aeruginosa* and treatment with PBS (white bars) or GLY (gray bars)

After infection with KEI 1025, GLY treatment reduced HMGB1 protein significantly at 5 (p<0.05), but not 3 days p.i. and did not differ in the normal cornea between groups (FIG. 7A). Treatment affected expression of antimicrobial peptides and upregulated the expression of CRAMP significantly in the normal, uninfected cornea (p<0.01) and at 3 days p.i. (p<0.05) with no difference between groups observed at 5 days p.i. (FIG. 7B). mBD2 protein (FIG. 7C) was significantly upregulated at 3 (p<0.001) and 5 (p<0.001) days p.i. and also was higher in the normal, contralateral uninfected eye (p<0.001). GLY vs PBS treatment did not differ significantly at 3 or 5 days p.i. or in the normal cornea for mBD3 protein (FIG. 7D). In all of FIGS. 7A-7D, the white bar shows result in PBS treated eye and the gray bar shows the result of treatment with GLY. All data for FIGS. 7A-7D are mean+SEM and were analyzed using a two-tailed Student t test (n=5/group/time).

GLY+/−rHMGB1

Mice infected with KEI 1025 were treated using both GLY and rHMGB1. Clinical scores (FIG. 8A) showed no significant differences between treatment groups at all times tested, however, slit lamp photographs showed enhanced opacity in rHMGB1 and GLY treated (FIG. 8C) vs GLY and PBS treated (FIG. 8B) corneas. Adding rHMGB1 to GLY treatment also significantly (p<0.001) enhanced bacterial plate count at 5 days p.i., but no difference was seen between groups at 3 days p.i. (FIG. 8D). Clinical score data were analyzed using a nonparametric Mann-Whitney U test. Horizontal lines indicate the median values. Magnification=8×; n=10/group/time. Plate count data are shown as mean+SEM and were analyzed using a two-tailed Student t test (n=5/group/time).

GLY Treatment Using Strain 19660

Severity of disease was graded (clinical scores) and photographs taken with a slit lamp following infection with cytotoxic ATCC strain 19660. GLY vs PBS treatment (FIG. 9A) showed reduced clinical scores that were significant both at 3 (p<0.05) and 5 (p<0.05), but not at 1 day p.i. Photographs taken with a slit lamp at 5 days p.i confirmed less disease, reduced opacity, in the GLY (FIG. 9C) compared with PBS treated eye (FIG. 9B). Horizontal lines indicate the median values. Data were analyzed using a nonparametric Mann-Whitney U test. Magnification=8×.

RT-PCR, ELISA, MPO Assay and Plate Count for ATCC Strain 19660

Figure 10A:
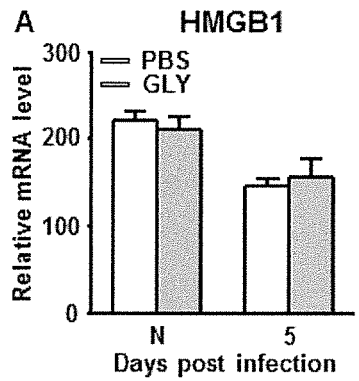
FIG. 10A is a graph showing relative HMGB1 mRNA levels in corneas analyzed by real-time RT-PCR after infection of corneas with *Pseudomonas aeruginosa* and treatment with PBS or GLY.
Figure 10B:
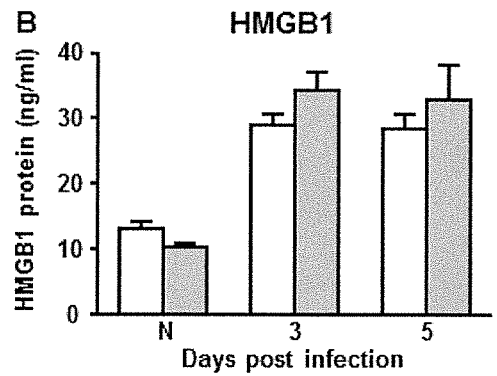
FIG. 10B is a graph showing HMGB1 levels in corneas after infection of corneas with *Pseudomonas aeruginosa* and treatment with PBS or GLY.
Figure 10C:
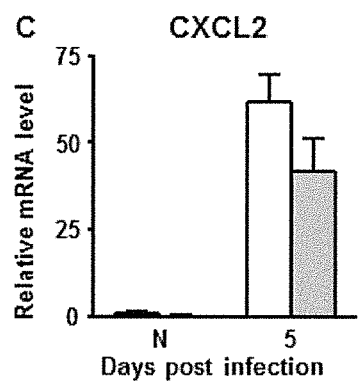
FIG. 10C is a graph showing relative CXCL2 mRNA levels in corneas analyzed by real-time RT-PCR after infection of in corneas with *Pseudomonas aeruginosa* and treatment with PBS or GLY.
Figure 10D:
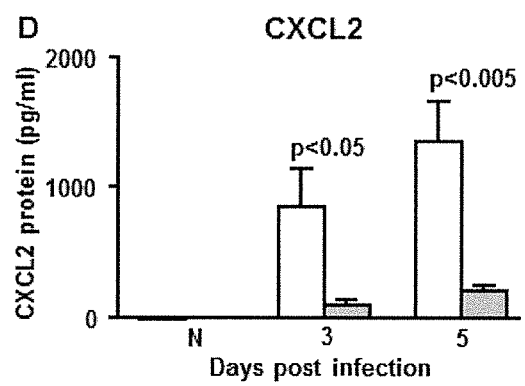
FIG. 10D is a graph showing CXCL2 levels in corneas after infection of corneas with *Pseudomonas aeruginosa* and treatment with PBS or GLY.
Figure 10E:
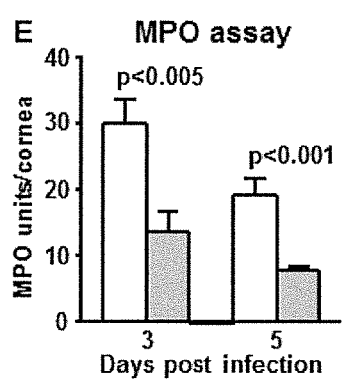
FIG. 10E is a graph showing the results of myeloperoxidase (MPO) assay in corneas after infection of corneas with *Pseudomonas aeruginosa* and treatment with PBS (white bars) or GLY (gray bars)
Figure 10F:
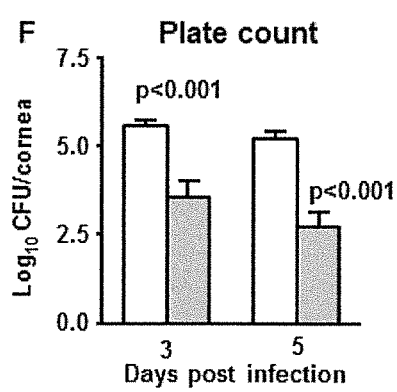
FIG. 10F is a graph showing the results of plate count showing bacterial load in the cornea after infection with *Pseudomonas aeruginosa* and treatment with PBS (white bars) or GLY (gray bars)

Relative mRNA levels for HMGB1 (FIG. 10A) were no different for both the uninfected, normal cornea and GLY treated infected cornea at 5 days p.i. Protein analysis confirmed the mRNA data, with no significant differences between the normal cornea or the two infected groups (FIG. 10B). mRNA levels of CXCL2 (FIG. 10C) were slightly, but not significantly decreased at 5 days p.i. after GLY vs PBS treatment. CXCL2 protein levels (FIG. 10D) were down-regulated significantly at 3 (p<0.05) and 5 (p<0.005) days p.i. in GLY vs PBS treated mice No differences in the normal cornea for mRNA or protein were detected between groups. An MPO assay (FIG. 10E) revealed a significant decrease in neutrophils in the cornea at 3 (p<0.005) and 5 (p<0.001) days p.i. after GLY vs PBS treatment. Bacterial load (FIG. 10F) was significantly reduced in the corneas of GLY vs PBS treated mice at both 3 (p<0.001) and 5 (p<0.001) days p.i. In all of FIGS. 10A-10F, the white bar shows result in PBS treated eye and the gray bar shows the result of treatment with GLY. All data are mean+SEM and were analyzed using a two-tailed Student t test (n=5/group/time).

GLY Post Treatment and Plate Count, KEI 1025

Ocular response to infection was graded (clinical scores) and photographs were taken with a slit lamp of the B6 mice infected with KEI 1025 and treated subconjunctivally (6 hours p.i.) and injected intraperitoneally (1 and 3 days p.i.) with GLY. Reduced clinical scores were seen only at 3 and 5 days p.i. after GLY vs PBS treatment (FIG. 11A). Photographs taken with a slit lamp documented decreased opacity in the GLY (FIG. 11C) compared with PBS treated eye (FIG. 11B). Nonetheless, despite the clinical appearance, bacterial load (FIG. 11D) was reduced significantly at both 3 (p<0.05) and 5 (p<0.001) days p.i. after GLY treatment. Data were analyzed using a nonparametric Mann-Whitney U test. Magnification=8×. All data are mean+SEM and were analyzed using a two-tailed Student t test (n=5/group/time).

Bacterial Growth and MIC

Figure 12A:
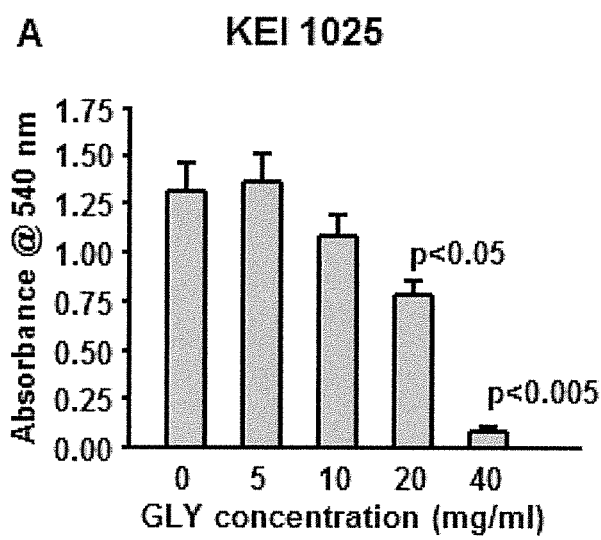
FIG. 12A is a graph showing absorbance values for *Pseudomonas aeruginosa* KEI 1025 cultures grown with GLY.
Figure 12B:
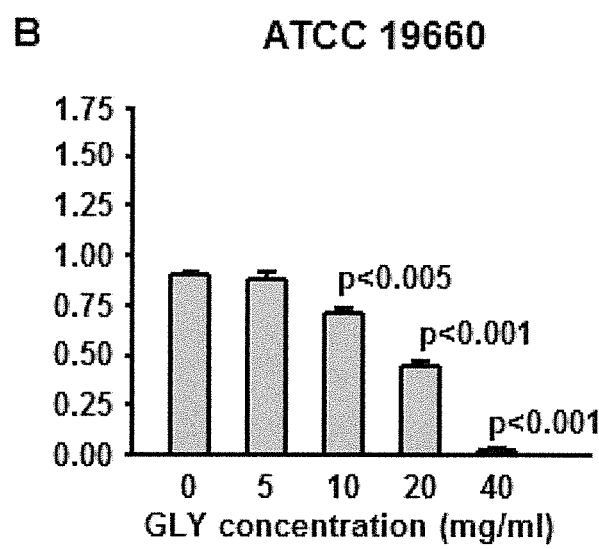
FIG. 12B is a graph showing absorbance values for *Pseudomonas aeruginosa* strain 19660 cultures grown with GLY.

For strain KEI 1025 (FIG. 12A), absorbance values were significantly reduced only for bacterial cultures grown with 20 (p<0.05) or 40 mg/ml (p<0.005) GLY. For strain 19660 (FIG. 12B), absorbance values were significantly reduced for bacterial cultures grown with 10 (p<0.01), 20 (p<0.001) or 40 mg/ml (p<0.001) of GLY. For both bacterial strains, $MIC_{50}$ and $MIC_{90}$ values of GLY were 20 and 40 mg/ml respectively. All data are mean+SEM and were analyzed using a two-tailed Student t test (n=3/group/strain).

Example 2

Mice

Eight-week-old female C57BL/6 (B6) mice were purchased from the Jackson Laboratory (Bar Harbor, Me.).

Bacterial Culture and Infection

*P. aeruginosa* strains, KEI 1025, a non-cytotoxic clinical isolate strain expressing exoT and exoS, and not expressing exoU, described in Estrellas P S, Jr., et al., Curr Eye Res. 2000; 20:157-165 (obtained from Kresge Eye Institute, Detroit, Mich.), and a cytotoxic strain, 19660, expressing exoU, described in Finck-Barbancon V, et al., Mol Microbiol. 1997; 25:547-557; and Fleiszig S M, et al., Infect Immun. 1997; 65:579-586 (obtained from American Type Culture Collection, ATCC, Manassas, Va.), were grown in peptone tryptic soy broth (PTSB) medium in a rotary shaker water bath at 37° C. and 150 rpm for 18 h to an optical density (measured at 540 nm) between 1.3-1.8. Bacterial cultures were pelleted by centrifugation at 5,500 g for 10 min. Pellets were washed once with sterile saline, re-centrifuged, re-suspended and diluted in sterile saline. Anesthetized (using anhydrous ethyl ether) mice were placed beneath a stereoscopic microscope at 40× magnification. The left cornea was scarified with three 1-mm incisions using a sterile $25^{5/8}$ gauge needle. The wounded corneal surface was topically treated with 5 µl containing $1\times10^7$ CFU/µl (KEI 1025) of the *P. aeruginosa* suspension.

Ocular Response to Bacterial Infection

An established corneal disease grading scale, described in detail in Hazlett L D, et al., Invest Ophthalmol Vis Sci. 1987; 28:1978-1985, was used to assign a clinical score value to each infected eye at 1, 3 and 5 days post infection (p.i.). Clinical scores were designated as: 0=clear or slight opacity, partially or fully covering the pupil; +1=slight opacity, fully covering the anterior segment; +2=dense opacity, partially or fully covering the pupil; +3=dense opacity, covering the entire anterior segment; and +4=corneal perforation or phthisis. Clinical scores were used to statistically compare disease severity and were accompanied by photographs using a slit lamp (5 days p.i.) to confirm and illustrate the response.

GLY Treatment.

The left eyes of B6 mice (n=5/group/time) were infected as above with *Pseudomonas* KEI 1025 strain. These infected B6 mice were treated by topical administration of GLY. *Pseudomonas aeruginosa* infected left cornea received 5 µL of GLY (20 µg/µL) topically beginning 6 (or 8) hours post infection and continued 2× daily for days 1-4 post infection.

Glycyrrhizin (GLY) Formulations
Subconjunctival injections: 5 µL of GLY (2 µg/µL)
Intraperitoneal injections: 100 µL of GLY (2 µg/µL)
Topical treatment: 5 µL of GLY (20 µg/µL)
GLY powder was dissolved in phosphate buffered saline (PBS) to make the above formulations.

FIGS. 13A-F shows results of GLY therapy at 8 hours (FIGS. 13A-C) and 6 hours (FIGS. 13D-F) after KEI 1025 infection FIG. 13A is a graph showing clinical scores, at 1, 3 and 5 days post-infection (p.i.) of the cornea with *Pseudomonas aeruginosa* KEI 1025, of mice treated topically with GLY beginning at 8 hours and at days 1, 2, 3 and 4 (twice each day) post-infection compared to mice treated with phosphate buffered saline (PBS).

FIG. 13B is an image at 5 days p.i. of the cornea of a mouse eye treated topically with PBS beginning at 8 hours and at days 1, 2, 3 and 4 (twice each day) post-infection.

FIG. 13C is an image at 5 days p.i. of the cornea of a mouse eye treated topically with GLY beginning at 8 hours and at days 1, 2, 3 and 4 (twice each day) post-infection.

FIG. 13D is a graph showing clinical scores at 1, 3 and 5 days post-infection (p.i.) of the cornea with *Pseudomonas aeruginosa* KEI 1025 of mice treated topically with GLY beginning at 6 hours and at days 1, 2, 3 and 4 (twice each day) post-infection compared to mice treated with phosphate buffered saline (PBS).

FIG. 13E is an image at 5 days p.i. of the cornea with *Pseudomonas aeruginosa* KEI 1025 of a mouse eye treated topically with PBS beginning at 6 hours and at days 1, 2, 3 and 4 (twice each day) post-infection.

FIG. 13F is an image at 5 days p.i. of the cornea with *Pseudomonas aeruginosa* KEI 1025 of a mouse eye treated topically with GLY beginning at 6 hours and at days 1, 2, 3 and 4 (twice each day) post-infection.

Figure 14A:
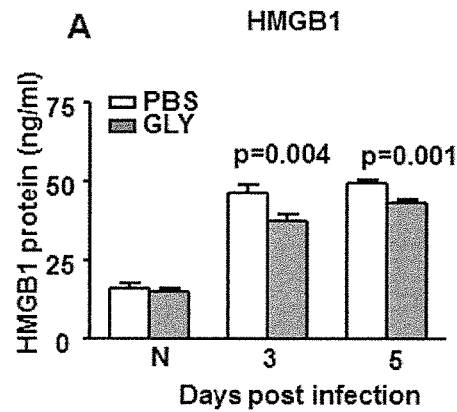
FIG. 14A is a graph showing results of an ELISA assay for HMGB1 in corneas at various times post-infection of the corneas with *Pseudomonas aeruginosa* where the mice were treated topically with PBS (white bars) or GLY (gray bars) beginning at 6 hours and at days 1-4 (×2 each day) post-infection.

FIG. 14A is a graph showing results of an ELISA assay for HMGB1 in corneas at various times post-infection of the corneas with *Pseudomonas aeruginosa* KEI 1025 where the mice were treated topically with PBS (white bars) or GLY (gray bars) beginning at 6 hours and at days 1, 2, 3 and 4 (twice each day) post-infection.

Figure 14B:
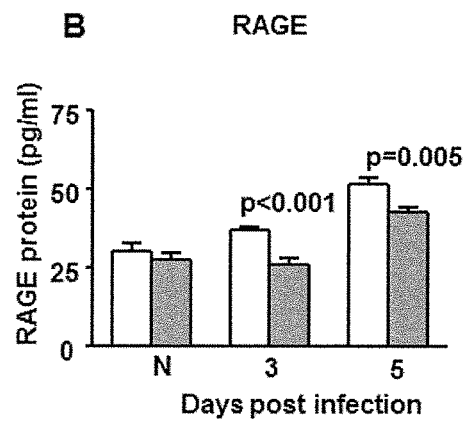
FIG. 14B is a graph showing results of an ELISA assay for RAGE in corneas at various times post-infection of the corneas where the mice were treated topically with PBS (white bars) or GLY (gray bars) beginning at 6 hours and at days 1-4 (×2 each day) post-infection with *Pseudomonas aeruginosa*.

FIG. 14B is a graph showing results of an ELISA assay for RAGE in corneas at various times post-infection of the corneas where the mice were treated topically with PBS (white bars) or GLY (gray bars) beginning at 6 hours and at days 1, 2, 3 and 4 (twice each day) post-infection with *Pseudomonas aeruginosa* KEI 1025.

Figure 14C:
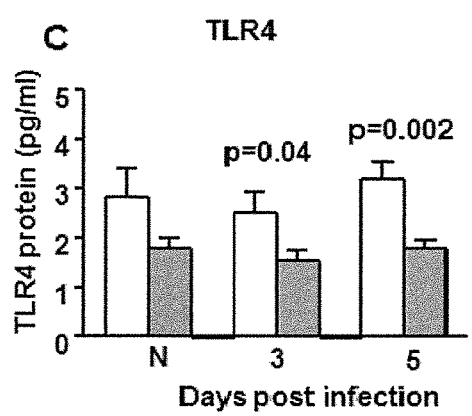
FIG. 14C is a graph showing results of an ELISA assay for TLR4 in corneas at various times post-infection of the corneas with *Pseudomonas aeruginosa* where the mice were treated topically with PBS (white bars) or GLY (gray bars) beginning at 6 hours and at days 1-4 (×2 each day) post-infection.

FIG. 14C is a graph showing results of an ELISA assay for TLR4 in corneas at various times post-infection of the corneas with *Pseudomonas aeruginosa* KEI 1025 where the mice were treated topically with PBS (white bars) or GLY (gray bars) beginning at 6 hours and at days 1, 2, 3 and 4 (twice each day) post-infection.

Figure 14D:
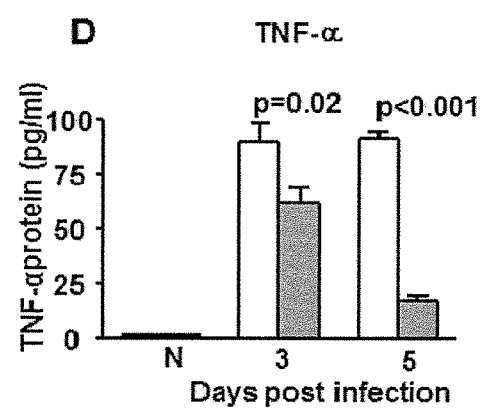
FIG. 14D is a graph showing results of an ELISA assay for TNF-alpha in corneas at various times post-infection of the corneas with *Pseudomonas aeruginosa* where the mice were treated with PBS (white bars) or GLY (gray bars) beginning at 6 hours and at days 1-4 (×2 each day) post-infection.

FIG. 14D is a graph showing results of an ELISA assay for TNF-alpha in corneas at various times post-infection of the corneas with *Pseudomonas aeruginosa* KEI 1025 where the mice were treated with PBS (white bars) or GLY (gray bars) beginning at 6 hours and at days 1, 2, 3 and 4 (twice each day) post-infection.

Figure 15A:
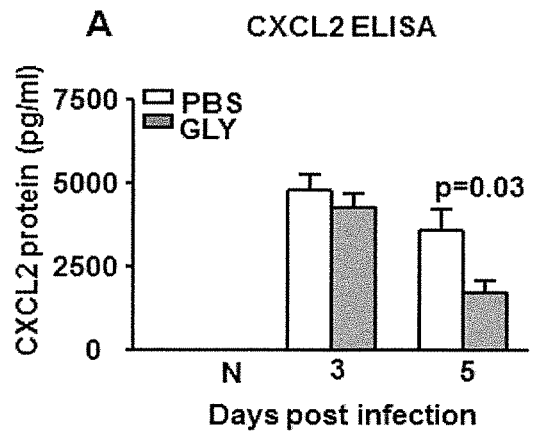
FIG. 15A is a graph showing results of an ELISA assay for CXCL2 in corneas at various times post-infection of the corneas with *Pseudomonas aeruginosa* where the mice were treated with PBS (white bars) or GLY (gray bars) beginning at 6 hours and at days 1-4 (×2 each day) post-infection.

FIG. 15A is a graph showing results of an ELISA assay for CXCL2 in corneas at various times post-infection of the corneas with *Pseudomonas aeruginosa* KEI 1025 where the mice were treated with PBS (white bars) or GLY (gray bars) beginning at 6 hours and at days 1, 2, 3 and 4 (twice each day) post-infection.

Figure 15B:
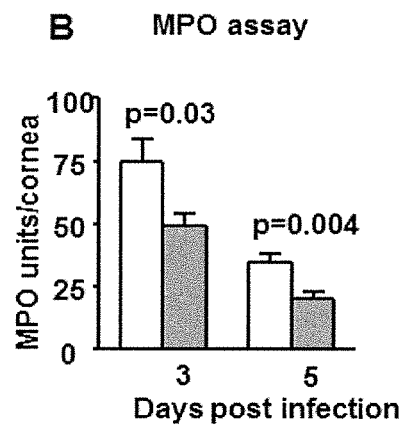
FIG. 15B is a graph showing results of an MPO assay in corneas at various times post-infection of the corneas with *Pseudomonas aeruginosa* where the mice were treated with PBS (white bars) or GLY (gray bars) at beginning at 6 hours and at days 1-4 (×2 each day) post-infection.

FIG. 15B is a graph showing results of an MPO assay in corneas at various times post-infection of the corneas with *Pseudomonas aeruginosa* KEI 1025 where the mice were treated with PBS (white bars) or GLY (gray bars) at beginning at 6 hours and at days 1, 2, 3 and 4 (twice each day) post-infection.

Figure 15C:
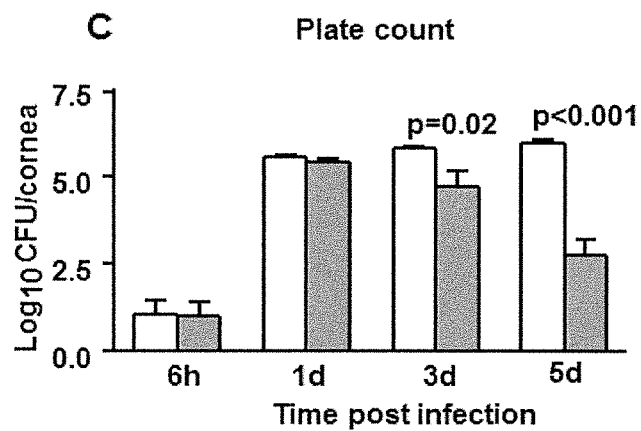
FIG. 15C is a graph showing results of a plate count assay of corneas at various times post-infection of the corneas with *Pseudomonas aeruginosa* where the mice were treated with PBS (white bars) or GLY (gray bars) at 6 hours and at days 1-4 (×2 each day) post-infection.

FIG. 15C is a graph showing results of a plate count assay of corneas at various times post-infection of the corneas with *Pseudomonas aeruginosa* KEI 1025 where the mice were treated with PBS (white bars) or GLY (gray bars) at 6 hours and at days 1, 2, 3 and 4 (twice each day) post-infection.

Figure 16A:
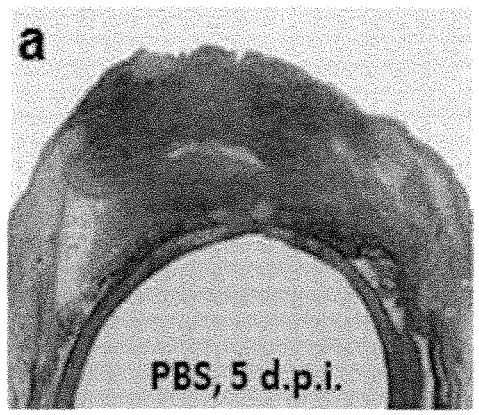
FIG. 16A is an image of a section (1.5 µm thick) at 5 days p.i. where the cornea was infected with *Pseudomonas aeruginosa*, stained with Richardson's stain for histopathological analysis; damage to the cornea and an increased cellular infiltrate is seen in the PBS treated eye; topical PBS treatment began at 6 hours p.i. and was given topically at days 1-4 (×2 each day) post-infection.

FIG. 16A is an image of a section (1.5 µm thick) at 5 days p.i. where the cornea was infected with *Pseudomonas aeruginosa* KEI 1025, stained with Richardson's stain for histopathological analysis; damage to the cornea and an increased cellular infiltrate is seen in the PBS treated eye; topical PBS treatment began at 6 hours p.i. and was given topically at days 1, 2, 3 and 4 (twice each day) post-infection.

Figure 16B:
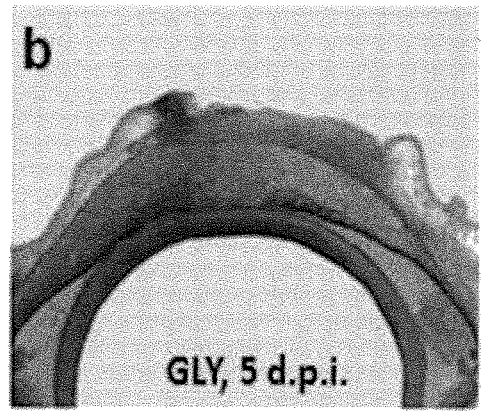
FIG. 16B is an image of a section (1.5 µm thick) at 5 days p.i. where the cornea was infected with *Pseudomonas aeruginosa*, stained with Richardson's stain for histopathological analysis; reduced damage to the cornea and a decreased cellular infiltrate is seen in the GLY vs PBS treated eye; topical GLY treatment began at 6 hours p.i. and was given topically at days 1-4 (×2 each day) post-infection. Initiation of treatment 6 hours after infection provided similar protection to the cornea as seen when treatment was initiated before infection.

FIG. 16B is an image of a section (1.5 µm thick) at 5 days p.i. where the cornea was infected with *Pseudomonas aeruginosa* KEI 1025, stained with Richardson's stain for histopathological analysis; reduced damage to the cornea and a decreased cellular infiltrate is seen in the GLY vs PBS treated eye; topical GLY treatment began at 6 hours p.i. and was given topically at days 1, 2, 3 and 4 (twice each day) post-infection. Initiation of treatment 6 hours after infection provided similar protection to the cornea as seen when treatment was initiated before infection.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of treating *Pseudomonas aeruginosa* infection of the cornea therapeutically in a subject, comprising:
administering a composition comprising an effective dose of glycyrrhizin, or a pharmaceutically acceptable salt, hydrate, solvate, amide, or isomer thereof to the subject, wherein no additional therapeutic agent is included in the composition, thereby reducing bacterial load in the cornea and thereby treating *Pseudomonas aeruginosa* infection of the cornea therapeutically in the subject.

2. The method of claim 1, wherein administering the effective dose of glycyrrhizin, or a pharmaceutically acceptable salt, hydrate, solvate, amide, or isomer thereof, comprises subconjunctival administration.

3. The method of claim 1, wherein administering the effective dose of glycyrrhizin, or a pharmaceutically acceptable salt, hydrate, solvate, amide, or isomer thereof, comprises topical administration to the cornea.

4. The method of claim 1, wherein administering the effective dose of glycyrrhizin, or a pharmaceutically acceptable salt, hydrate, solvate, amide, or isomer thereof, comprises systemic administration.

5. The method of claim 1, wherein administering the effective dose of glycyrrhizin, or a pharmaceutically acceptable salt, hydrate, solvate, amide, or isomer thereof, comprises parenteral administration.

6. The method of claim 1, wherein administering the effective dose of glycyrrhizin, or a pharmaceutically acceptable salt, hydrate, solvate, amide, or isomer thereof, comprises intravenous administration.

7. The method of claim 1, wherein the effective dose of glycyrrhizin, or a pharmaceutically acceptable salt, hydrate, solvate, amide, or isomer thereof, is administered to the subject within 24 hours of a traumatic ocular surface event wherein the traumatic ocular surface event caused a *Pseudomonas aeruginosa* infection of the cornea.

8. The method of claim 1, wherein the subject is human.

9. The method of claim 1, wherein the subject is a horse.

* * * * *